United States Patent [19]
Morelli et al.

[11] Patent Number: 5,919,752
[45] Date of Patent: *Jul. 6, 1999

[54] PERFUMES HAVING ODOR LONGEVITY BENEFITS

[75] Inventors: Joseph Paul Morelli; Scott William Waite, both of Cincinnati; Stacy Renee Hertenstein, Mason; Mark Robert Sivik, Fairfield, all of Ohio

[73] Assignee: Procter & Gamble, Cincinnati, Ohio

[ * ] Notice: This patent is subject to a terminal disclaimer.

[21] Appl. No.: 09/028,823

[22] Filed: Feb. 24, 1998

Related U.S. Application Data

[60] Provisional application No. 60/044,561, Apr. 24, 1997.
[51] Int. Cl.$^6$ .............. A61K 7/46; A61K 7/00; A61K 6/00; A62C 13/62
[52] U.S. Cl. .............. 512/1; 239/302; 424/401; 512/25; 512/26; 512/27
[58] Field of Search .................. 512/1, 25, 26, 512/27; 424/401; 239/302

[56] References Cited

U.S. PATENT DOCUMENTS

| | | | |
|---|---|---|---|
| 5,342,584 | 8/1994 | Fritz et al. | 422/124 |
| 5,378,468 | 1/1995 | Suffis et al. | 424/401 |
| 5,562,642 | 10/1996 | Smith et al. | 604/289 |
| 5,686,405 | 11/1997 | Lebreton et al. | 512/2 |

*Primary Examiner*—Shelley A. Dodson
*Assistant Examiner*—Marina Lamm
*Attorney, Agent, or Firm*—Richard S. Echler, Sr.; Kim W. Zerby; Jacobus C. Rasser

[57] ABSTRACT

The present invention relates to perfume or fine fragrance compositions inter alia perfumes, colognes, eau de toilettes, and after shave lotions, comprising pro-accord compounds which release their fragrance raw material components on a delayed basis therefore providing sustained fragrance levels to the user. Typically the pro-accords are comprised of orthoesters, ketals, acetals, orthocarbonates which release two or more fragrance raw materials upon hydrolysis. The present invention also relates to an article of manufacture comprising a first pro-accord containing reservoir and a second fragrance raw material reservoir and a means for admixing and applying the perfume material.

16 Claims, No Drawings

PERFUMES HAVING ODOR LONGEVITY BENEFITS

This application claim benefit of Provisional application 06,044,561 filed Apr. 24, 1997.

FIELD OF THE INVENTION

The present invention relates to fine fragrance perfumes, eau de toilettes, colognes, after-shave lotions and other fragrance-containing personal perfumery compositions for application directly to skin, said compositions having increased odor longevity benefits. The odor longevity benefits are produced by combining top and middle note pro-fragrances alone or in combination with other fragrance raw materials, said pro-fragrances releasing volatile top and middle notes at a predetermined rate upon contact with skin thereby either maintaining the initial perfume characteristics for extended periods or evolving a new fragrance characteristic that evolves over time.

BACKGROUND OF THE INVENTION

Humans have applied scents and fragrances to their skin since antiquity. Originally these aesthetically pleasing materials were commonly isolated in raw form as resins, gums or essential oils from natural sources, inter alia, the bark, roots, leaves and fruit of indigenous plants. These resins, gums, and oils were directly applied to the body or diluted with water or other solvent, including in some cases, wine. With the advent of modern chemistry, individual components responsible for the odor properties of these resins, gums and oils were isolated and subsequently characterized. Modern perfumery involves the artful compounding of fragrance materials to achieve novel fragrance compositions having defined "characteristics".

Many modem fragrances are no longer derived from natural sources but are synthesized by modem chemical methods as highly pure fragrance raw materials (FRM). These FRM's are currently formulated to produce fine perfumes, colognes, eau de toilettes, after-shave lotions, and other personal fragrance compositions. Those skilled in the art of preparing these fragrance-containing compositions have categorized fragrances into three types based on their relative volatility; top, middle, and base notes. In addition, fragrances are categorized by the odor they produce; some of these descriptors are broad and others are relatively specific. For example, "floral" is a term which connotes odors associated with flowers while the term "lilac" is more specific. Descriptors used by those skilled in the art of perfumes and fine fragrances are inter alia "rose", "floral", "green", "citrus", "spicy", "honey", and "musk".

Top, middle, and base notes each serve a different purpose in the blending of fragrances and when properly formulated produce a "balanced fragrance" composition. Based on volatility, these notes are described by those skilled in the art as: the base notes having the most long lasting aroma; the middle notes, have a medium volatility; and the top notes are the most volatile. Key to successfully formulating a fragrance-containing composition is the precise balance between these three groups of materials producing a fragrance-containing composition that diffuses during its evaporation in a manner which has an aesthetic quality.

It is recognized by those skilled in the art that descriptors which relate to aesthetic perceptions such as "top", "middle" and "base" notes are relative terms. A FRM categorized as a top note by one formulator usually has the identical classification among most other Perfumers. The same is true for the middle and base notes, however, occasionally one formulator may classify a given fragrance raw material as a middle note rather than a top note, or vice versa, but this fact does not diminish the utility of a given compound or its absolute identity. Top, middle and base notes are now combined in a reproducible manner to produce perfumes, colognes, after-shave lotions, eau de toilettes, etc. for application to skin, which have unique and pleasant odor characteristics. Yet apart from this pleasant fragrance, a perfume, cologne, or eau de toilette must meet a number of technical requirements. It must be sufficiently strong, it must be persistent, and it must retain its "essential character" throughout its period of evaporation. It is to these latter two requirements that the present invention is directed.

Due to the uneven rate of evaporation of the components which comprise a fine perfume or fragrance, the initial fragrance may be quite different than the aroma perceived several hours later. This problem is solved in many different ways by the user. One method is to "load up" on the perfume initially and rely on the natural evaporation rate to diminish the fragrance to a suitable level several hours later when the desired effect is needed. Another method which is used is to continually renew the fragrance by reapplying small amounts of the perfume to the skin at short time intervals. Neither of these solutions is adequate to overcome the diminishing level of top and middle notes over time. In fact, base notes which are present over a protracted period by virtue of their low volatility, begin to accumulate with each "refreshing" of perfume. After some time these base notes overwhelm the other fragrance notes and destroy the original fragrance balance.

BACKGROUND ART

In addition to the above-cited references, the following relate to the subject matter of fragrance ingredients. U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 3,849,326 Jaggers et al., issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/14827 published May 23, 1996; and WO 95/16660 published Jun. 22, 1995. In addition, P. M. Muller, D. Lamparsky *Perfumes Art, Science, & Technology* Blackie Academic & Professional, (New York, 1994) is included herein by reference.

SUMMARY OF THE INVENTION

The present invention meets the aforementioned needs in that it has been surprisingly discovered that a perfume or fine fragrance can be formulated which provides the user with a more enduring fragrance level and more sustained fragrance balance. What is meant by a "more enduring fragrance level" is that the fragrance raw materials which comprise the scent or fragrance accords of the perfume or fine fragrance are present upon the skin for a longer period of time than if the fragrance raw materials had been applied as an admixture. What is meant by a "more sustained fragrance balance" is that the relative proportion of top, middle, and base notes is more effectively maintained for a period of time longer than if the fragrance raw materials had been applied as an admixture. This increased fragrance endurance and balance is achieved by mitigating the loss of volatile top and middle note fragrance raw materials due to evaporation. The top and middle character notes are delivered via pro-accord compounds which do not begin to hydrolyze and release the fragrance raw materials until the scent-containing material is applied to human skin.

The first aspect of the present invention relates to a perfume or fine fragrance composition applied to skin having increased fragrance retention and fragrance longevity, said compositions are inter alia perfumes, fine fragrances, fragrance oils, colognes, eau de toilettes, or after shave lotions, comprising:

A) a pro-accord component comprising:
  i) one or more pro-accords formed from at least one fragrance raw material, said pro-accord releasing upon hydrolysis at least two fragrance raw materials selected from the group consisting of primary, secondary, and tertiary alcohols, aldehydes, ketones, esters, carbonates, and mixtures thereof, provided each pro-accord:
     a) is formed from at least one fragrance raw material having a molecular weight greater than or equal to about 100 g/mol;
     b) has a molecular weight greater than or equal to about 300 g/mol;
     c) has a molecular weight at least two times greater than the lowest molecular weight fragrance raw material which comprises said pro-accord;
     d) has a fragrance release half-life of greater than or equal to 0.1 hours at pH 5.3 and less than or equal to 12 hours at pH 2.5 when measured in $NaH_2PO_4$ buffer;
  ii) the balance carriers, stabilizers, and other adjunct ingredients whereby said pro-accord component is provided with an amount of reserve alkalinity equal to at least 0.001 molar NaOH; and
B) a fragrance raw material component comprising:
  i) a mixture of base note fragrances;
  ii) one or more top and middle note fragrances;
  iii) the balance carriers, fixatives, and other adjunct ingredients.

It is also an aspect of the present invention to provide an article of manufacture which serves to deliver the perfumes and fine fragrances of the present invention. These articles can comprise one or more reservoirs for storage of the fragrance materials until they are delivered to the skin of the user. In addition the articles of the present invention can comprise reservoirs which comprise a material having an alkaline or a neutralized surface component.

Another aspect of the present invention is to provide pro-accords which provide fragrance raw materials at a level wherein the "odor value" or "level of noticeability" is greater than or equal to 1 as define herein.

It is a further aspect of the present invention to provide a means by which a perfume or fine fragrance having a "first fragrance characteristic" has this scent replaced by a "second evolving fragrance characteristic".

It is a yet further aspect of the present invention to provide a means for delivering the perfume or fine fragrance material wherein the pro-accord material is admixed with other perfume components prior to delivery to the skin of the user. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (°C.) unless otherwise specified. All documents cited are in relevant part, incorporated herein by reference.

DETAILED DESCRIPTION OF THE INVENTION

It has now been surprisingly found that certain fragrance raw materials or perfume components can be converted into a releasable "pro-fragrance" form which allows for the controlled release of the parent fragrance material upon exposure to human skin. By understanding the molecular weight requirements as well the "Fragrance Release Half-life", $t_{1/2}$, disclosed within the present invention, the formulator can choose the precise "pro-fragrance" form to achieve controlled release of the volatile ingredients and therefore maintain the "initial fragrance profile" for extended periods of time. In addition, by formulating the proper pro-fragrances new characteristics can be caused to evolve over the period of use. These discoveries are applicable to perfumes, colognes, after-shaves, and other fragrance-containing materials in use today.

The releasable pro-fragrances suitable for use in the present invention, have a molecular weight requirement that has not been realized by others who have previously formulated pro-fragrance materials. This molecular weight requirement relates to one or more aspects of the pro-fragrance, for example, in substantivity differences, volatility differences, etc. For example, U.S. Pat. No. 5,378,468 Suffis et al., issued Jan. 3, 1995, describes pro-fragrance containing compositions, inter alia, deodorants, lotions, and creams, which do not produce fragrances until contacted with skin. However, this reference falls short of teaching that certain pro-fragrances or pro-fragrance forms, although suitable for use in controlling the release rate of fragrance raw materials on the short term, are not themselves suitable for use in fine perfumes, colognes, eau de toilettes, etc. wherein extended benefits for the wearer are desired. For example, certain pro-perfume forms are too volatile for formulation according to the present invention because they themselves evaporate as fast as, or faster than the fragrance materials themselves. In addition, many volatile pro-fragrances outside the scope of the present invention have their own distinguishable odor that is significantly different that the odor of the released fragrance. It is therefore not uncommon to have a pro-fragrance incompatible with the other perfume components. Many pro-fragrances have their own "fragrance" and it is common that the "characteristic" of the pro-fragrance odor is not within the same class of odors as the target composition. For example, the pro-fragrance may have an "herbal" odor but the released fragrance is "rose-like" in character.

Pro-perfumes which are acid labile (i.e., release their fragrance materials in an acid containing medium such as the acid mantle of skin) can be suitably formulated into highly alkaline matrices which typically comprise roll-on deodorants, creams, lotions, etc. Many of the fragrance ingredients which comprise perfumes, colognes, eau de toilettes, after-shave lotions, etc. are not suitable for inclusion in an alkaline pH environment, for example, many of the commonly known fragrance notes are esters and they are susceptible to rapid hydrolysis at pH levels much above neutrality.

The present invention provides releasable pro-fragrances which are activated upon contact with the acid mantle of the skin. The pro-fragrances of the present invention are acetals, ketals, orthoesters and orthocarbonates having a molecular weight of at least 300 g/mol. The present invention also provides fine perfumes, eau de toilettes, and colognes that comprise a pro-fragrance component in a releasable form such that the fragrance is released at a rate which provides extended fragrance benefits together with a component comprising free fragrances and other middle and base notes that are not stable to alkaline pH. The present invention also provides a method for selecting pro-fragrances which release their fragrances in a controlled manner allowing for a second subsequent fragrance "characteristic" to develop over time as replacement for the initial fragrance "characteristic".

The present invention also provides for pro-accords which are capable of releasing fragrance raw materials at a rate which is of utility to the formulator of fine fragrances or perfumes. For example, as described further herein below, the pro-accords of the present invention have a fragrance release half-life of greater than or equal to 0.1 hours at pH 5.3 and less than or equal to 12 hours at pH 2.5. In addition, the fragrance raw materials are released at a level wherein the odor value of said fragrance raw material is greater than 1.

For the purposes of the present invention the terms "perfume" and "fine fragrance" are essentially synonymous and are used collectively or interchangeably throughout the present specification and are taken to mean the more concentrated forms of fragrance-containing compositions. Aspects of the present invention which apply to "perfumes" will therefore apply equally to "fine fragrances" and vice versa. typically, colognes, eau de toilettes, after shaves, and other fragrance-containing embodiments are perfumes or fine fragrances which have a greater degree of dilution, usually by a volatile carrier such as ethanol.

The present invention relates to perfume and fine fragrance compositions having scent or odor longevity benefits wherein these benefits are achieved by controllably releasing the fragrance components that comprise the perfume or fine fragrance. The present invention also relates to changing the "characteristic notes" of a fragrance composition by releasing new fragrance notes as the original notes evaporate or diffuse from the skin. For example, a "melon note" fragrance composition may be suitably conveyed to a "rose note" fragrance by the evaporation of the original "melon characteristics" and subsequent release of the new "rose characteristics".

Fine perfumes typically comprise components which react with human olfactory sites resulting in what is known as "fragrance". Typical molecules which comprise perfume fragrances are linear and cyclic alkenes (i.e., terpenes), primary, secondary and tertiary alcohols, nitrites, ethers, saturated and unsaturated aldehydes, esters, ketones, and mixtures thereof. Each of these perfume fragrances can be classified according to its volatility into one of three categories; "top note", "middle note", and "base note".

For the purposes of the present invention "top note" fragrances are defined as "fragrances having a high vapor pressure, and when applied to a paper sachet, vaporization takes place within 2 hours, and no scent remains; essentially, the initial impression of the perfume formulation is provided by top notes".

For the purposes of the present invention "middle note" fragrances are defined as "fragrances having a medium vapor pressure, and when applied to a paper sachet, the scent remains from about 2 to about 6 hours; essentially, middle notes provide the skeleton of the perfume formulation".

For the purposes of the present invention "base note" fragrances are defined as "fragrances having a low vapor pressure and high retentivity, and when applied to a paper sachet, the scent remains for more than about 6 hours; essentially, base notes provide the characteristic of the perfume formulation.

The terms "top note", "middle note", and "base note" are well recognized by those skilled in the art of fragrance-containing compositions. However, reference to a specific fragrance raw material as a "top note" within the present invention does mean that others skilled in the art of fragrance-containing compositions may not categorized the same ingredient as a "middle note". The same applies to fragrance raw materials referred to as "middle notes" and "base notes".

Mixtures of fragrance materials are known by those skilled in the art of fragrances and perfumes as "accords". The term "accord" as used herein is defined as "a mixture of two or more 'fragrance raw materials' which are artfully combined to impart a pleasurable scent, odor, essence, or fragrance characteristic". For the purposes of the present invention "fragrance raw materials" are herein defined as compounds having a molecular weight of at least 100 g/mol and which are useful in imparting an odor, fragrance, essence, or scent either alone or in combination with other "fragrance raw materials".

Typically "fragrance raw materials" comprise inter alia alcohols, ketones, aldehydes, esters, ethers, nitrites, and alkenes such as terpenes. A listing of common "fragrance raw materials" can be found in various reference sources, for example, "Perfume and Flavor Chemicals", Vols. I and II; Steffen Arctander Allured Pub. Co. (1994) and "Perfumes: Art, Science and Technology"; Müller, P. M. and Lamparsky, D., Blackie Academic and Professional (1994) both incorporated herein by reference.

For example, but not by way of limitation, the fragrance accords released by the pro-accords of the present invention have a "heart", "character", or "note" which is described as inter alia rose, jasmin, lilac, lily of the valley, violet, orange, peach, watermelon, and lemon. The accord may be further "modified" or "twisted" by the use of modifier top or middle notes which, as an additional benefit afforded by the present invention, can be incorporated into the pro-accord. For example, a "rose essence" may be combined with a "green" modifier to "shift the fragrance accord character".

The pro-accords of the present invention are comprised of one or more fragrance raw materials. The fragrance raw materials selected to comprise the final released accord are converted into a chemical species or reactive chemical form which releases the fragrance raw materials once the pro-accord is subjected to the proper hydrolysis conditions. Depending upon the particular embodiment chosen, the hydrolysis conditions may range from the acid mantle of human skin, to the nascent moisture which comprises air. These chemically modified forms of the fragrance raw materials are the "pro-accords" of the present invention. One principle aspect of the present invention is the ability of pro-accords described herein to deliver more than one fragrance raw material when the "pro-accord" has been formed from only one fragrance raw material. All of the pro-accords of the present invention are capable of releasing at least two fragrance raw materials (hereinafter "binary accord") upon deposition, for example, onto skin or hair. There are two types of pro-accords; "symmetrical" pro-accords and "unsymmetrical" pro-accords each described herein further below.

Molecular Weight

The pro-accords of the present invention generally have a molecular weight of at least 300 g/mol, preferably greater than 325 g/mol, more preferably greater than 350 g/mol. It is also a condition of the present invention that the final molecular weight of the pro-accord is at least 2 times, preferably at least 2.25 times, more preferably 2.5 times, most preferably at least 2.75 times the molecular weight of the lowest fragrance material component.

For the purposes of the present invention, only fragrance raw materials having a molecular weight of at least 100 g/mol are considered "fragrance raw materials". Therefore, low molecular weight materials inter alia methanol, ethanol, methyl acetate, ethyl acetate, and methyl formate which are common components of fragrance accords are excluded from the class of compounds defined herein as "fragrance raw materials". However, the formulator may wish to deliver these lower molecular weight materials (less than a molecular weight of 100 g/mol) as carriers, astringents, diluents, balancers, or as other suitable adjunct materials.

By way of illustration and not limitation, the pro-accord tris(geranyl) orthoformate is considered, for the purposes of the present invention to be formed from three equivalents of geraniol. This pro-accord releases the binary accord geraniol/geranyl formate. This pro-accord has a molecular weight of approximately 472 g/mol. The lowest molecular weight fragrance raw material which is a component of tris(geranyl)orthoformate is geraniol which has a molecular weight of approximately 154 g/mol. Therefore tris(geranyl) orthoformate has a molecular weight greater than 3 times the molecular weight of the lowest molecular weight fragrance raw material component (geraniol) and hence is a most preferred pro-accord.

For the purposes of the present invention substituted or unsubstituted alkyleneoxy units are defined as moieties having the formula:

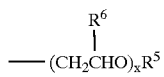

wherein $R^5$ is hydrogen, methyl, and mixtures thereof, $R^6$ is hydrogen, methyl, ethyl, and mixtures thereof; the index x is from 1 to about 20.

For the purposes of the present invention substituted or unsubstituted alkyleneoxyalkyl are defined as moieties having the formula:

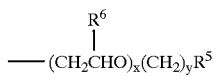

wherein $R^5$ is hydrogen, $C_1$–$C_{18}$ alkyl, and mixtures thereof; $R^6$ is hydrogen, methyl, ethyl, and mixtures thereof; the index x is from 1 to about 20 and the index y is from 2 to about 30.

For the purposes of the present invention substituted or unsubstituted alkylenearyl units are defined as moieties having the formula:

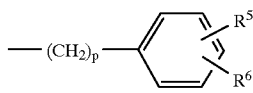

wherein $R^5$ and $R^6$ are each independently hydrogen, hydroxy, nitrilo, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, alkylamino, and mixtures thereof, p is from 1 to about 34.

For the purposes of the present invention substituted or unsubstituted aryloxy units are defined as moieties having the formula:

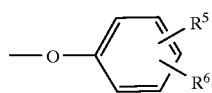

wherein $R^5$ and $R^6$ are each independently hydrogen, hydroxy, nitro, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, alkylamino, and mixtures thereof.

For the purposes of the present invention substituted or unsubstituted alkyleneoxyaryl units are defined as moieties having the formula:

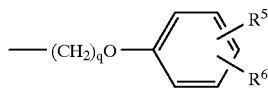

wherein $R^5$ and $R^6$ are each independently hydrogen, hydroxy, nitro, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, alkylamino, and mixtures thereof, q is from 1 about 34.

For the purposes of the present invention substituted or unsubstituted oxyalkylenearyl units are defined as moieties having the formula:

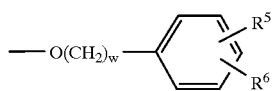

wherein $R^5$ and $R^6$ are each independently hydrogen, hydroxy, nitro, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, alkylamino, and mixtures thereof, w is from 1 about 34.

Orthoesters

One class of preferred compounds useful as pro-accords according to the present invention are orthoesters having the formula:

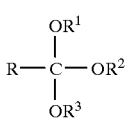

wherein hydrolysis of the orthoester releases fragrance raw material components according to the following scheme:

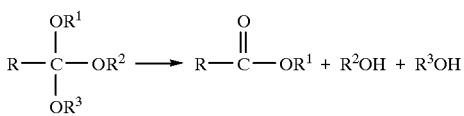

wherein R is hydrogen, $C_1$–$C_8$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, preferably the moieties which substitute the aryl units are alkyl moieties, and mixtures thereof, preferably R is hydrogen, methyl, ethyl, and phenyl. $R^1$, $R^2$ and $R^3$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl; $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof. By the term "substituted" herein is meant "compatible moieties which replace a hydrogen atom". Non-limiting examples of substituents are hydroxy, nitro, halogen, nitro, carboxyl (—CHO; —CO$_2$H; —CO$_2$R'; —CONH$_2$; —CONHR'; —CONR'$_2$; wherein R'is $C_1$–$C_{12}$ linear or branched alkyl), amino, $C_1$–$C_{12}$ mono- and dialkylamino, and mixtures thereof.

Non-limiting examples of $R^1$, $R^2$ and $R^3$ are methyl, 2,4-dimethyl-3-cyclohexene-1-methyl (Floralol), 2,4-dimethyl cyclohexane methyl (Dihydro floralol), 5,6-dimethyl-1-methylethenyl-bicyclo[2.2.1]hept-5-ene-2-methyl (Arbozol), 2,4,6-trimethyl-3-cyclohexene-1-methyl (Isocyclo geranyl), 4-(1-methylethyl)cyclohexylmethyl (Mayol), α-3,3-trimethyl-2-norboranylmethyl, 1,1-dimethyl-1-(4-methylcyclohex-3-enyl)methyl, ethyl, 2-phenylethyl, 2-cyclohexylethyl, 2-(o-methylphenyl)ethyl, 2-(m-methylphenyl)ethyl, 2-(p-methylphenyl)ethyl, 6,6-dimethylbicyclo[3.1.1]hept-2-ene-2-ethyl (nopyl), 2-(4-methylphenoxy)ethyl, 3,3-dimethyl-Δ$^2$-β-norboranylmethyl, 2-methyl-2-cyclohexylethyl, 1-(4-isopropylcyclohexyl)ethyl, 1-phenyl-1-hydroxyethyl, 1,1-dimethyl-2-phenylethyl, 1,1-dimethyl-2-(4-methylphenyl) ethyl, propyl, 1-phenylpropyl, 3-phenylpropyl, 2-phenylpropyl (Hydrotropic Alcohol), 2-(cyclododecyl)-propan-1-yl (Hydroxyambran), 2,2-dimethyl-3-(3-methylphenyl)propan-1-yl (Majantol), 2-methyl-3-phenylpropyl, 3-phenyl-2-propen-1-yl (cinnamyl alcohol), 2-methyl-3-phenyl-2-propen-1-yl (methylcinnamyl alcohol), α-n-pentyl-3-phenyl-2-propen-1-yl (α-amylcinnamyl alcohol), ethyl-3-hydroxy-3-phenyl propionate, 2-(4-methylphenyl)-2-propyl, butyl, 3-methylbutyl, 3-(4-methylcyclohex-3-ene)butyl, 2-methyl-4-(2,2,3-trimethyl-3-cyclopenten-1-yl)butyl, 2-ethyl-4-(2,2,3-trimethylcyclopent-3-enyl)-2-buten-1-yl, 3-methyl-2-buten-1-yl, 2-methyl-4-(2,2,3-trimethyl-3-cyclopenten-1-yl)-2-buten-1-yl, 3-hydroxy-2-butanone, ethyl 3-hydroxybutyrate, 4-phenyl-3-buten-2-yl, 2-methyl-4-phenylbutan-2-yl, 4-(4-hydroxyphenyl)butan-2-one, 4-(4-hydroxy-3-methoxyphenyl)butan-2-one, pentyl, cis-3-pentenylt 3-methylpentyl, 3-methyl-3-penten-1-yl, 2-methyl-4-phenylpentyl (Pamplefleur), 3-methyl-5-phenylpentyl (Phenoxanyl), 2-methyl-5-phenylpentyl, 2-methyl-5-(2,3-dimethyltricyclo[2.2.1.0(2,6)]hept-3-yl)-2-penten-1-yl (santalyl), 4-methyl-1-phenyl-2-pentyl, (1-methyl-bicyclo[2.1.1]hepten-2-yl)-2-methylpent-1-en-3-yl, 3-methyl-1-phenylpent-3-yl, 1,2-dimethyl-3-(1-methylethenyl)cyclopent-1-yl, 2-isopropyl-4-methyl-2-hexenyl, cis-3-hexen-1-yl, trans-2-hexen-1-yl, 2-isopropenyl-5-methyl-4-hexen-1-yl (Lavandulyl), 2-ethyl-2-prenyl-3-hexenyl (silwanol), 2-ethylhexyl, 1-hydroxymethyl-4-isopropenyl-1-cyclohexenyl (Dihydrocuminyl), 1-methyl-4-isopropenylcyclohex-6-en-2-yl (carvenyl), 6-methyl-3-isopropenylcyclohex-1-yl, 1-methyl-4-isopropenylcyclohex-3-yl, 4-iso-propyl -1-methylcyclohex-3-yl, 4-tert-butylcyclohexyl, 2-tert-butylcyclohexyl, 2-tert-butyl-4-methylcyclohexyl, 4-isopropylcyclohexyl, 4-methyl-1-(1-methylethyl)-3-cyclohexen-1-yl, 2-(5,6,6-trimethyl-2-norbornyl) cyclohexyl, isobornylcyclohexyl, 3,3,5-trimethylcyclohexyl, 1-methyl-4-isopropylcyclohex-3-yl (menthol), 1,2-dimethyl-3-(1-methylethyl)cyclohexan-1-yl, heptyl, 2,4-dimethylhept-1-yl, 2,4-dimethyl-2,6-heptandienyl, 6,6-dimethyl-2-oxymethylbicyclo[3.1.1]hept-2-en-1-yl (myrtenyl), 4-methyl-2,4-heptadien-1-yl, 3,4,5,6, 6-pentamethyl-2-heptyl, 3,6-dimethyl-3-vinyl-5-hepten-2-yl, 6,6-dimethyl-3-hydroxy-2-methylenebicyclo[3.1.1]-heptyl, 1,7,7-trimethylbicyclo[2.2.1]hept-2-yl, 2,6-dimethylhept-2-yl, 2,6,6-trimethylbicyclo[1.3.3]hept-2-yl, octyl, 2-octenyl, 2-methyloctan-2-yl, 2-methyl-6-methylene-7-octen-2-yl (myrcenyl), 7-methyloctan-1-yl, 3,7-dimethyl-6-octenyl, 3,7-dimethyl-7-octenyl, 3,7-dimethyl-6-octen-1-yl (citronellyl), 3,7-dimethyl-2,6-octadien-1-yl (geranyl), 3,7-dimethyl-2,6-octadien-1-yl (neryl), 3,7-dimethyl-1,6-octadien-3-yl (linalyl), 3,7-dimethyloctan-1-yl (pelagryl), 3,7-dimethyloctan-3-yl (tetrahydrolinalyl), 2,4-octadien-1-yl, 3,7-dimethyl-6-octen-3-yl, 2,6-dimethyl-7-octen-2-yl, 2,6-dimethyl -5,7-octadien-2-yl, 4,7-dimethyl-4-vinyl-6-octen-3-yl, 3-methyloctan-3-yl, 2,6-dimethyloctan-2-yl, 2,6-dimethyloctan-3-yl, 3,6-dimethyloctan-3-yl, 2,6-dimethyl-7-octen-2-yl, 2,6-dimethyl-3,5-octadien-2-yl (mugyl), 3-methyl-1-octen-3-yl, 7-hydroxy-3,7-dimethyloctanalyl, 3-nonyl, 6,8-dimethylnonan-2-yl, 3-(hydroxymethyl)-2-nonanone, 2-nonen-1-yl, 2,4-nonadien-1-yl, 2,6-nonadien-1-yl, cis-6-nonen-1-yl, 3,7-dimethyl-1,6-nonadien-3-yl, decyl, 9-decenyl, 2-benzyl-M-dioxa-5-yl, 2-decen-1-yl, 2,4-decadien-1-yl, 4-methyl-3-decen-5-yl, 3,7,9-trimethyl-1,6-decadien-3-yl (isobutyl linallyl), undecyl, 2-undecen-1-yl, 10-undecen-1-yl, 2 -dodecen-1-yl, 2,4-dodecadien-1-yl, 2,7, 11-trimethyl-2,6,10-dodecatrien-1-yl (farnesyl), 3,7,11-trimethyl-1,6,10,-dodecatrien-3-yl, 3,7,11,15-tetramethylhexadec-2-en-1-yl (phytyl), 3,7,11,15-tetramethylhexadec-1-en-3-yl (iso phytol), benzyl, p-methoxybenzyl (anisyl), para-cymen-7-yl (cuminyl), 4-methylbenzyl, 3,4-methylenedioxybenzyl, 2-(methyl) carboxy-1-hydroxyphenyl, 2-(benzyl)carboxy-1-hydroxyphenyl, 2-(cis-3-hexenyl)-carboxy-1-hydroxyphenyl, 2-(n-pentyl)carboxy-1-hydroxyphenyl, 2-(2-phenylethyl)carboxy-1-hydroxyphenyl, 2-(n-hexyl) carboxy-1-hydroxyphenyl, 2-methyl-5-isopropyl-1-hydroxyphenyl, 4-ethyl-2-methoxyphenyl, 4-allyl-2-methoxy-1-hydroxyphenyl (eugenyl), 2-methoxy-4-(1-propenyl)-1-hydroxyphenyl (isoeugenyl), 4-allyl-2,6-dimethoxy-1-hydroxyphenyl, 4-tert-butyl-1-hydroxyphenyl, 2-ethoxy-4-methyl-1-hydroxyphenyl, 2-methyl-4-vinyl-1-hydroxyphenyl, 2-isopropyl-5-methyl-1-hydroxyphenyl (thymyl), 2-(isopentyl)carboxy-1-hydroxyphenyl, 2-(ethyl) carboxy-1-hydroxyphenyl, 6-(methyl)carboxy-2,5-dimethyl-1,3-dihydroxyphenyl, 5-methoxy-3-methyl-1-hydroxyphenyl, 2-tert-butyl-4-methyl-1-hydroxyphenyl, 1-ethoxy-2-hydroxy-4-propenylphenyl, 4-methyl-1-hydroxyphenyl, 4-hydroxy-3-methoxybenzaldehyde, 2-ethoxy-4-hydroxybenzaldehyde, decahydro-2-naphthyl, 2,5,5-trimethyl-octahydro-2-naphthyl, 1,3,3-trimethyl-2-norbornyl (fenchyl), 3a,4,5,6,7,7a-hexahydro-2,4-dimethyl- 4,7-methano-1H-inden-5-yl, 3a,4,5,6,7,7a-hexahydro-3,4-dimethyl-4,7-methano-1H-inden-5-yl, 2-methyl-2-vinyl-5-(1-hydroxy-1-methylethyl)tetrahydrofuranyl, β-caryophyllenyl, and mixtures thereof.

Also $R^1$, $R^2$, or $R^3$ units may serve to link two pro-accords for the purpose of providing greater substantivity. An example of pro-accord linking by a diol has the following formula:

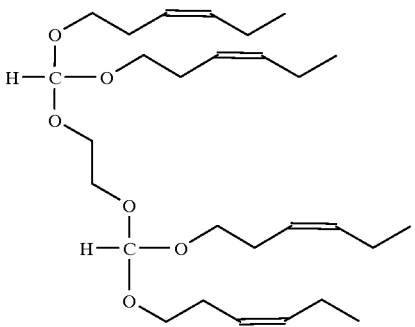

In addition to the releasable alcohols listed herein above, orthoesters according to the present invention are also cyclic orthoesters which are comprised from at least one diol having the formula:

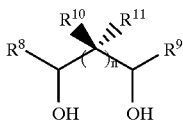

wherein $R^8$, $R^9$, $R^{10}$, and $R^{11}$ are each in dependently hydrogen, $C_1$–$C_{20}$ linear or branched alkyl, $C_1$–$C_{20}$ linear or branched alkenyl, $C_1$–$C_{20}$ linear, branched or cyclic alkylenecarboxy, $C_1$–$C_{20}$ linear, branched, or cyclic carboxyalkyl, $C_1$–$C_{20}$ linear or branched alkyleneamino, $C_1$–$C_{20}$ linear or branched aminoalkyl, $C_1$–$C_{20}$ linear, branched, or cyclic alkylenecarboxamido, $C_1$–$C_{20}$ linear or branched carboxamidoalkyl, alkyleneoxy having the formula:

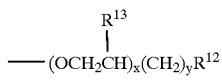

wherein $R^{12}$ is hydrogen or methyl; $R^{13}$ is hydrogen or $C_1$–$C_2$ alkyl; n is from 0 to 4, x is from 1 to about 20, y is from 0 to about 20.

Orthoester Releasable Components: Hydrolysis of the orthoesters of the present invention have two types of releasable components, namely alcohols and esters. Hydrolysis of an orthoester will yield two equivalents of releasable alcohol, preferably a primary or secondary alcohol and one equivalent of releasable ester. The released ester, when taken together with the released alcohol, forms a binary fragrance accord. For example tri-geranyl orthoformate releases the binary accord geraniol/geranyl formate.

Preferred esters which are releasable components of the orthoesters of the present invention included but are not limited to geranyl formate, citronellyl formate, phenylethyl formate, phenoxyethyl formate, trans-2-hexenyl formate, cis-3-hexenyl formate, cis-6-nonenyl formate, 9-decenyl formate, 3,5,5-trimethylhexyl formate, 3-methyl-5-phenylpentanyl formate, 6-methylheptan-2-yl formate, 4-(2,2,6-trimethyl-2-cyclohexen-1-yl)-3-buten-2-yl formate, 3-methyl-5-(2,2,3-trimethyl-3-cyclopenten-1-yl)-4-penten-2-yl formate, 4-isopropylcyclohexyleth-2-yl formate, 6,8-dimethylnonan-2-yl formate, decahydro-β-naphthyl formate, 4-isopropylcyclohexylmethyl formate, linalyl formate, lavandulyl formate, citronellyl formate, α-terpinyl formate, nopyl formate, isobornyl formate, bornyl formate, isobornyl formate, guaiyl formate, 2-tert-butylyclohexyl formate, 4-tert-butylcyclohexyl formate, decahydro-p-naphthyl formate, menthyl formate, p-menthanyl formate, neryl formate, cinnamyl formate, ethyl acetate, butyl acetate, isoamyl acetate, hexyl acetate, 3,5,5-trimethylhexyl acetate, geranyl acetate, citronellyl acetate, phenylethyl acetate, phenoxyethyl acetate, trans-2-hexenyl acetate, cis-3-hexenyl acetate, cis-6-nonenyl acetate, 9-decenyl acetate, 3-methyl-5-phenylpentanyl acetate, 6-methyl-heptan-2-yl acetate, 4-(2,2,6-trimethyl-2-cyclohexen-1-yl)-3-buten-2-yl acetate, 3-methyl-5-(2,2,3-trimethyl-3-cyclopenten-1-yl)-4-penten-2-yl acetate, decahydro-β-naphthyl acetate, menthyl acetate, benzyl acetate, 4-isopropylcyclohexyleth-2-yl acetate, 6,8-dimethylnonan-2-yl acetate, 1-phenylethyl acetate, 4-isoproylcyclo-hexylmethyl acetate, linalyl acetate, lavandulyl acetate, citronellyl acetate, α-terpinyl acetate, nopyl acetate, isobornyl acetate, bornyl acetate, isobornyl acetate, guaiyl acetate, 2-tert-butylyclohexyl acetate, 4-tert-butylcyclohexyl acetate, decahydro-β-naphthyl acetate, menthyl acetate, p-menthanyl acetate, neryl acetate, cinnamyl acetate, ethyl propionate, ethyl butyrate, butyl butyrate, isoamyl butyrate, hexyl butyrate, cis-3-hexenyl butyrate, cis-3-hexenyl isobutyrate, ethyl isovalerate, 2-methylbutyrate, ethyl hexanoate, 2-propenyl hexanoate, ethyl heptanoate, 2-propenyl heptanoate, ethyl octanoate, ethyl 2-trans-4-cis-decadienoate, methyl 2-nonynoate, benzyl propionate, benzyl isovalerate, phenylethyl isobutyrate, phenylethyl isovalerate, α,α-dimethyl phenylethyl butyrate, methyl benzoate, hexyl benzoate, benzyl benzoate, ethyl phenylacetate, geranyl phenylacetate, 1-phenylethyl phenylacetate, methyl cinnamate, benzyl cinnamate, phenylethyl cinnamate, geranyl propionate, geranyl isobutyrate, geranyl isovalerate, linalyl propionate, linalyl buryrate, linalyl isobutyrate, citronellyl propionate, citronellyl isobutyrate, citronellyl isovalerate, citronellyl tiglate, allyl 3-cyclohexylpropionate, methyl dihydrojasmonate, methyl 2-hexyl-3-oxocyclopentane-carboxylate, and mixtures thereof.

Non-limiting examples of alcohols suitably released by the hydrolysis of the orthoester pro-accords include methanol, 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), 2,4,6-trimethyl-3-cyclohexene-1-methanol (Isocyclo geraniol), 4-(1-methylethyl)cyclohexanemethanol (Mayol), α-3,3-trimethyl-2-norborane methanol, 1,1-dimethyl-1-(4-methylcyclohex-3-enyl)methanol, ethanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4- methylphenoxy)ethanol, 3,3-dimethyl-Δ²-β-norbornane ethanol, 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, n-propanol, 2-propanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), (α-n-pentyl-3-phenyl-2-propen-1-ol (α-amyl-cinnamyl alcohol), ethyl-3-hydroxy-3-phenyl propionate, 2-(4-methylphenyl)-2-propanol, n-butanol, 2-butanol, 3-methylbutanol, 3-(4-methylcyclohex-3-ene) butanol, 2-methyl-4-(2,2,3-trimethyl-3-cyclopenten-1-yl) butanol, 2-ethyl-4-(2,2.3-trimethyl-cyclopent-3-enyl)-2-buten-1ol, 3-methyl-2-buten-1-ol, 2-methyl-4-(2,2,3-trimethyl-3-cyclopenten-1-yl)-2-1-ol, 3-hydroxy-2-butanone, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)butan-2-one, pentanol, cis-3-pentenol, 3-methyl-pentanol, 3-methyl-3-penten-1-ol, 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0(2,6)]hept-3-yl)-2-penten-1-ol (santalol), 4-methyl-1-phenyl-2-pentanol, (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol, 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol, 4-isopropyl-cyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1,2-dimethyl-3-(1-methylethyl)cyclohexan-1-ol, heptanol, 2,4-dimethylheptan-1-ol, 2,4-dimethyl-2,6-heptandienol, 6,6-dimethyl-2-oxymethylbicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1]heptan -2-ol, 2,6-dimethylheptan-2-ol, 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-1,6-octadien-3-ol (linalool), 3,7-dimethyloctan-1ol (pelagrol), 3,7-dimethyloctan-3-ol (tetrahydrolinalool), 2,4-octadien-1-ol, 3,7-dimethyl-6-octen-3-ol, 2,6-dimethyl-7-octen-2-ol, 2,6-dimethyl-5,7-octadien-2-ol, 4,7-dimethyl-4-vinyl-6-octen-3-ol, 3-methyloctan-3-ol, 2,6-dimethyloctan-2-ol, 2.6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linallol), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol, 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydrozytoluene, 4-hydroxy-3-methoxybenzaldehyde, 2-ethoxy-4-hydroxybenzaldehyde, decahydro-2-naphthol, 2,5,5-trimethyl-octahydro -2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl) tetrahydrofuran, β-caryophyllene alcohol, and mixtures thereof.

Preferred alcohols released by the orthoesters of the present invention are 4-(1-methylethyl) cyclohexanemethanol (mayol), 2,4-dimethyl-3-cyclohexen-1-ylmethanol (floralol), 2,4-dimethylcyclohex-1-ylmethanol (dihydrofloralol), 2,4,6-trimethyl-3-cyclohexen-1-ylmethanol (isocyclogeraniol), 2-phenylethanol, 1-(4-isopropylcyclohexyl)ethanol (mugetanol), 2-(o-methylphenyl)ethanol (ortho-hawthanol), 2-(m-methylphenyl)ethanol (meta-hawthanol), 2-(p-methylphenyl)-ethanol (para-hawthanol), 2,2-dimethyl-3-(3-methylphenyl)propan-1-ol (majantol), 3-phenyl-2-propen-1-ol (cinnamic alcohol), 2-methyl-4-(2,2,3-trimethyl -3-cyclopenten-1-yl)-2-buten-1-ol (santalaire), 3-methyl-5-phenylpentan-1-ol (phenoxanol), 3-methyl-5-(2,2,3-trimethyl-3-cyclopenten-1-yl)-4-penten-2-ol (ebanol), 2-methyl-4-phenylpentan-1-ol (pamplefleur), cis-3-hexen-1-ol, 3,7-dimethyl-6-octen-1-ol (citronellol), 3,7-dimethyl-2,6-octadien-1-ol (geraniol, nerol or mixtures thereof), 7-methoxy-3,7-dimethyloctan-2-ol (osyrol), 6,8-dimethylnonan-2-ol, cis-6-nonen-1-ol, 2,6-nonadien-1-ol, 4-methyl-3-decen-5-ol (undecavertol), benzyl alcohol, 2-methoxy-4-(1-propenyl)phenol (isoeugenol), 2-methoxy-4-(2-propenyl)phenol (eugenol), 4-hydroxy-3-methoxybenzaldehyde (vanillin), and mixtures thereof.

Non-limiting examples of orthoester pro-fragrances according to the present invention are tris-geranyl orthoformate, tris(cis-3-hexen-1-yl)orthoformate, tris(phenylethyl)orthoformate, bis(citronellyl) ethyl orthoacetate, tris(citronellyl)orthoformate, tris(cis-6-nonenyl)orthoformate, tris(phenoxyethyl)orthoformate, tris(geranyl, neryl)orthoformate (70:30 geranyl:neryl), tris(9-decenyl)orthoformate, tris(3-methyl-5-phenylpentanyl)orthoformate, tris(6-methylheptan-2-yl)orthoformate, tris([4-(2,2,6-trimethyl-2-cyclohexen-1-yl)-3-buten-2-yl] orthoformate, tris[3-methyl-5-(2,2,3-trimethyl-3-cyclopenten-1-yl)-4-penten-2-yl]orthoformate, trismenthyl orthoformate, tris(4-isopropylcyclohexylethyl-2-yl) orthoformate, tris-(6,8-dimethylnonan-2-yl)orthoformate, tris-phenylethyl orthoacetate, tris(cis-3-hexen-1-yl) orthoacetate, tris(cis-6-nonenyl)orthoacetate, tris-citronellyl orthoacetate, bis(geranyl)benzyl orthoacetate, tris(geranyl) orthoacetate, tris(4-isopropylcyclohexylmethyl) orthoacetate, tris(benzyl)orthoacetate, tris(2,6-dimethyl-5-heptenyl)orthoacetate, bis(cis-3-hexen-1-yl)amyl orthoacetate, and neryl citronellyl ethyl orthobutyrate. Orthoester pro-accords can be used to deliver inter alia binary fragrance accords, fragrance accords having a "binary characteristic" accord component in combination with a modifier accord, and fragrance accords comprising astringents, fixatives, or diluents.

Another class of orthoesters suitable for use as pro-accords according to the present invention are cyclic orthoesters having the formula:

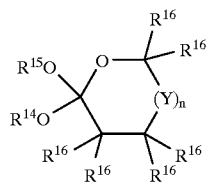

wherein $R^{14}$ and $R^{15}$ are derived from the same fragrance raw material alcohols described herein above, each $R^{16}$ is independently hydrogen, $C_1$–$C_{22}$ linear or branched alkyl, $C_2$–$C_{22}$ linear or branched alkenyl, $C_6$–$C_{22}$ substituted or unsubstituted aryl, and mixtures thereof, Y is —$CR^{17}R^{18}$—, C=O, and mixtures thereof, wherein $R^{17}$ and $R^{18}$ are independently hydrogen, hydroxyl, nitro, nitro, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^{17}$ and $R^{18}$ can be taken together to form a spiroannulated ring or taken together with any $R^{16}$ to form a fused ring, said spiroannulated or fused ring having from 3 to 8 carbons and optionally one or more heteroatoms in said ring, said ring further optionally substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; n is from 0 to 3.

Acetals and ketals

Another class of compound useful as pro-accords according to the present invention are acetals and ketals having the formula:

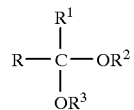

wherein hydrolysis of the acetal or ketal releases one equivalent of aldehyde or ketone and two equivalents of alcohol according to the following scheme:

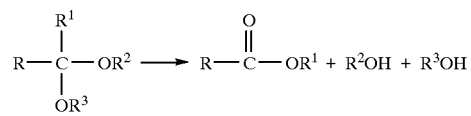

wherein R is $C_1$–$C_{20}$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, preferably the moieties which substitute the aryl units are alkyl moieties, and mixtures thereof. $R^1$ is hydrogen, R, or in the case wherein the pro-accord is a ketal, R and $R^1$ can be taken together to form a ring. $R^2$ and $R^3$ are independently selected from the group consisting of $C_5$–$C_{20}$ linear, branched, or substituted alkyl; $C_4$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof. By the term "substituted" herein is meant "compatible moieties which replace a hydrogen atom". Non-limiting examples of substituents are hydroxy, nitro, halogen, nitro, carboxyl (—CHO; —$CO_2$H; —$CO_2$R'; —$CONH_2$; —CONHR'; —$CONR'_2$; wherein R' is $C_1$–$C_{12}$ linear or branched alkyl), amino, $C_1$–$C_{12}$ mono- and dialkylamino, and mixtures thereof.

Non-limiting examples of $R^2$ and $R^3$ include methyl, 2,4-dimethyl-3-cyclohexene -1-methyl (Floralol), 2,4-dimethyl cyclohexane methyl (Dihydro floralol), 5,6-dimethyl-1-methylethenyl-bicyclo[2.2.1]hept-5-ene-2-methyl (Arbozol), 2,4,6-trimethyl-3-cyclohexene-1-methyl (Isocyclo geranyl), 4-(1methylethyl)cyclohexylmethyl (Mayol), α-3,3-trimethyl-2-norboranylmethyl, 1,1-dimethyl-1-(4-methylcyclohex-3-enyl)methyl, ethyl, 2-phenylethyl, 2-cyclohexylethyl, 2-(o-methylphenyl)ethyl, 2-(m-methylphenyl)ethyl, 2-(p-methylphenyl)ethyl, 6,6-dimethylbicyclo[3.1.1]hept-2-ene-2-ethyl (nopyl), 2 -(4-methylphenoxy)ethyl, 3,3-dimethyl-$\Delta^2$-β-norboranylmethyl, 2-methyl-2-cyclohexylethyl, 1-(4-isopropylcyclohexyl)ethyl, 1phenyl-1-hydroxyethyl, 1,1-dimethyl-2-phenylethyl, 1,1-dimethyl-2-(4-methylphenyl) ethyl, propyl, 1-phenylpropyl, 3-phenylpropyl, 2-phenylpropyl (Hydrotropic Alcohol), 2-(cyclododecyl)-propan-1-yl (Hydroxyambran), 2,2-dimethyl-3-(3-methylphenyl)propan-1-yl (Majantol), 2-methyl-3-phenylpropyl, 3-phenyl-2propen-1-yl (cinnamyl alcohol), 2-methyl-3-phenyl-2-propen-1-yl (methylcinnamyl alcohol), α-n-pentyl-3-phenyl-2-propen-1-yl (α-amylcinnamyl alcohol), ethyl-3-hydroxy-3-phenyl propionate, 2-(4-methylphenyl)-2-propyl, butyl, 3-methylbutyl, 3-(4-methylcyclohex-3-ene)butyl, 2-methyl-4-(2,2,3-trimethyl-3-cyclopenten-1-yl)butyl, 2-ethyl-4-(2,2,3-trimethylcyclopent-3-enyl)-2-buten-1-yl, 3-methyl-2-buten-1-yl, 2-methyl-4-(2,2,3-trimethyl-3-cyclopenten-1-yl)-2-buten-1-yl, 3-hydroxy-2-butanone, ethyl 3-hydroxybutyrate, 4-phenyl-3-buten-2-yl, 2-methyl-4-phenylbutan-2-yl, 4-(4-hydroxyphenyl)butan-2-one, 4-(4-hydroxy-3-methoxyphenyl)butan-2-one, pentyl, cis-3-pentenyl, 3-methylpentyl, 3-methyl-3-penten-1-yl, 2-methyl-4-phenylpentyl (Pamplefleur), 3-methyl-5-phenylpentyl (Phenoxanyl), 2-methyl-5-phenylpentyl, 2-methyl-5-(2,3-dimethyltricyclo[2.2.1.0(2,6)]hept-3-yl)-2-penten-1-yl (santalyl), 4-methyl-1-phenyl-2-pentyl, (1-methyl-bicyclo[2.1.1]hepten-2-yl)-2-methylpent-1-en-3-yl, 3-methyl-1-phenylpent-3-yl, 1,2-dimethyl-3-(1-methylethenyl)cyclopent-1-yl, 2-isopropyl-4-methyl-2-hexenyl, cis-3-hexen-1-yl, trans-2-hexen-1-yl, 2-isopropenyl-5methyl-4-hexen-1-yl (Lavandulyl), 2-ethyl-2-prenyl-3-hexenyl (silwanol), 2-ethylhexyl, 1-hydroxymethyl-4-isopropenyl-1-cyclohexenyl (Dihydrocuminyl), 1-methyl-4-isopropenylcyclohex-6-en-2-yl (carvenyl), 6-methyl-3-isopropenylcyclohex-1-yl, 1-methyl-4-isopropenylcyclohex-3-yl, 4-iso-propyl-1-methylcyclohex-3-yl, 4-tert-butylcyclohexyl, 2-tert-butylcyclohexyl, 2-tert-butyl-4-methylcyclohexyl, 4-isopropylcyclohexyl, 4-methyl-1-(1-methylethyl)-3-cyclohexen-1-yl, 2-(5,6,6-trimethyl-2-norbornyl)cyclohexyl, isobornylcyclohexyl, 3,3,5-trimethylcyclohexyl, 1-methyl-4-isopropylcyclohex-3-yl (menthol), 1,2-dimethyl-3-(1-methylethyl)cyclohexan-1-yl, heptyl, 2,4-dimethylhept-1-yl, 2,4-dimethyl-2,6-heptandienyl, 6,6-dimethyl-2-oxymethylbicyclo[3.1.1]hept-2-en-1-yl (myrtenyl), 4-methyl-2,4 -heptadien-1-yl, 3,4,5,6,6-pentamethyl-2-heptyl, 3,6-dimethyl-3-vinyl-5-hepten-2-yl, 6,6-dimethyl-3-hydroxy-2-methylenebicyclo[3.1.1]-heptyl, 1,7,7-trimethylbicyclo[2.2.1]hept-2-yl, 2,6-dimethylhept-2-yl, 2,6,6-trimethylbicyclo[1.3.3]hept-2-yl, octyl, 2-octenyl, 2-methyloctan-2-yl, 2-methyl-6-methylene-7-octen-2-yl (myrcenyl), 7-methyloctan-1-yl, 3,7-dimethyl-6-octenyl, 3,7-dimethyl-7-octenyl, 3,7-dimethyl-6-octen-1-yl (citronellyl), 3,7-dimethyl-2,6-octadien-1-yl (geranyl), 3,7-dimethyl-2,6-octadien-1-yl (neryl), 3,7-dimethyl-1,6-octadien-3-yl (linalyl), 3,7-dimethyloctan-1-yl (pelagryl), 3,7-dimethyloctan-3-yl (tetrahydrolinalyl), 2,4-octadien-1-yl, 3,7-dimethyl-6-octen-3-yl, 2,6-dimethyl-7-octen-2-yl, 2,6-dimethyl-5,7-octadien-2-yl, 4,7-dimethyl-4-vinyl-6-octen-3-yl, 3-methyloctan-3-yl, 2,6-dimethyloctan-2-yl, 2,6-dimethyloctan-3-yl, 3,6-dimethyloctan-3-yl, 2,6-dimethyl-7-octen-2-yl, 2,6-dimethyl-3,5-octadien-2-yl (mugyl), 3-methyl-1-octen-3-yl, 7-hydroxy-3,7-dimethyloctanalyl, 3-nonyl, 6,8-dimethylnonan-2-yl, 3-(hydroxymethyl)-2-nonanone, 2-nonen-1-yl, 2,4-nonadien-1-yl, 2,6-nonadien-1-yl, cis-6-nonen-1-yl, 3,7-dimethyl-1,6-nonadien-3-yl, decyl, 9-decenyl, 2-benzyl-M-dioxa-5-yl, 2-decen-1-yl, 2,4-decadien-1-yl, 4-methyl-3-decen-5-yl, 3,7,9-trimethyl-1,6-decadien-3-yl (isobutyl linallyl), undecyl, 2-undecen-1-yl, 10-undecen-1-yl, 2-dodecen-1-yl, 2,4-dodecadien-1-yl, 2,7,11-trimethyl-2,6,10-dodecatrien-1-yl (farnesyl), 3,7,11-trimethyl-1,6,10,-dodecatrien-3-yl, 3,7,11,15-tetramethylhexadec-2-en-1-yl (phytyl), 3,7,11,15-tetramethylhexadec-1-en-3-yl (iso phytol), benzyl, p-methoxybenzyl (anisyl), para-cymen-7-yl (cuminyl), 4-methylbenzyl, 3,4-methylenedioxybenzyl, 2-(methyl)carboxy-1-hydroxyphenyl, 2-(benzyl)carboxy-1-hydroxyphenyl, 2-(cis-3-hexenyl)-carboxy-1-hydroxyphenyl, 2-(n-pentyl)carboxy-1-hydroxyphenyl, 2-(2-phenylethyl)carboxy-1-hydroxyphenyl, 2-(n-hexyl)carboxy-1-hydroxyphenyl, 2-methyl-5-isopropyl-1-hydroxyphenyl, 4-ethyl-2-methoxyphenyl, 4-allyl-2-methoxy-1-hydroxyphenyl (eugenyl), 2-methoxy-4-(1-propenyl)-1-hydroxyphenyl (isoeugenyl), 4-allyl-2,6-dimethoxy-1-hydroxyphenyl, 4-tert-butyl-1-hydroxyphenyl, 2-ethoxy-4-methyl-1-hydroxyphenyl, 2-methyl-4-vinyl-1-hydroxyphenyl, 2-isopropyl-5-methyl-1-hydroxyphenyl (thymyl), 2-(isopentyl)carboxy-1-hydroxyphenyl, 2-(ethyl)carboxy-1-hydroxyphenyl, 6-(methyl)carboxy-2,5-dimethyl-1,3-dihydroxyphenyl, 5-methoxy-3-methyl-i-hydroxyphenyl, 2 -tert-butyl-4-methyl-1-hydroxyphenyl, 1-ethoxy-2-hydroxy-4-propenylphenyl, 4-methyl-1-hydroxyphenyl, 4-hydroxy-3-methoxybenzaldehyde, 2-ethoxy-4-hydroxybenzaldehyde, decahydro-2-naphthyl, 2,5,5-trimethyl-octahydro-2-naphthyl, 1,3,3-trimethyl-2-norbornyl (fenchyl), 3a,4,5,6,7,7a-hexahydro-2,4-dimethyl-4,7-methano-1H-inden-5-yl, 3a,4,5,6,7,7a-hexahydro-3,4-dimethyl-4,7-methano-1H-inden-5-yl, 2-methyl-2-vinyl-5-(1-hydroxy-1-methylethyl)tetrahydrofuranyl, β-caryophyllenyl, and mixtures thereof.

Acetal Releasable Components: The acetals of the present invention have two types of releasable components, namely alcohols and aldehydes. Hydrolysis of an acetal will yield two equivalents of releasable alcohol and one equivalent of releasable aldehyde. The released aldehyde, when taken together with the released alcohol, forms a binary fragrance accord. For example bis(cis-3-hexenyl) vanillin acetal releases the binary accord vanillin/cis-3-hexenol.

When $R^1$ is hydrogen the pro-accords are capable of releasing an aldehyde component. Preferred aldehydes which are releasable components of the acetals of the present invention include but are not limited to phenylacetaldehyde, p-methyl phenylacetaldehyde, p-isopropyl phenylacetaldehyde, methylnonyl acetaldehyde, phenylpropanal, 3-(4-t-butylphenyl)-2-methyl propanal (Lilial), 3-(4-t-butylphenyl)propanal (Bourgeonal), 3-(4-methoxyphenyl)-2-methylpropanal (Canthoxal), 3-(4-isopropylphenyl)-2-methylpropanal (Cymal), 3-(3,4-methylenedioxyphenyl)-2-methylpropanal (Helional), 3-(4-ethylpheny)-2,2-dimethylpropanal (Floralozone), phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (Melonal), 2,4-heptadienal, octanal, 2-octenal, 3,7-dimethyloctanal, 3,7-dimethyl-2,6-octadien-1-al, 3,7-dimethyl-1,6-octadien-3-al, 3,7-dimethyl-6-octenal (citronellal), 3,7-dimethyl-7-hydroxyoctan-1-al (hydroxy citronellal), nonanal, 6-nonenal, 2,4-nonadienal, 2,6-nonadienal, decanal, 2-methyl decanal, 4-decenal, 9-decenal, 2,4-decadienal, undecanal, 2-methyldecanal, 2-methylundecanal, 2,6,10- trimethyl-9-undecenal (Adoxal), undec-10-enyl aldehyde, undec-8-enanal, dodecanal, tridecanal, tetradecanal, anisaldehyde, bourgenonal, cinnamic aldehyde, α-amylcinnamaldehyde, α-hexyl cinnamaldehyde, methoxy-cinnamaldehyde, isocyclocitral, citronellyl oxyacet-aldehyde, cortexaldehyde, cumminic aldehyde, cyclamen aldehyde, florhydral, heliotropin, hydrotropic aldehyde, vanillin, ethyl vanillin, benzaldehyde, p-methyl benzaldehyde, 3,4-dimethoxybenzaldehyde, 3- and 4-(4-hydroxy-4-methyl-pentyl)-3-cyclohexene-1-carboxaldehyde (Lyral), 2,4-dimethyl-3-cyclohexene-1-carboxaldehyde (Triplal), 1-methyl-3-(4-methylpentyl)-3-cyclohexencarboxaldehyde (Vernaldehyde), p-methylphenoxyacetaldehyde (Xi aldehyde), and mixtures thereof.

More preferably the aldehydes released by the acetals of the present invention are 4-(4-hydroxy-4-methylpentyl)-3-cyclohexene-1-carboxaldehyde (lyral), phenylacetaldehyde, methylnonyl acetaldehyde, 2-phenylpropan-1-al (hydrotropaldehyde), 3-phenylprop-2-en-1-al (cinnamaldehyde), 3-phenyl-2-pentylprop-2-en-1-al (α-amylcinnamaldehyde), 3-phenyl-2-hexylprop-2-enal(α-hexylcinnamaldehyde), 3-(4-isopropylphenyl)-2-methylpropan-1-al (cyclamen aldehyde), 3-(4-ethylphenyl)-2,2-dimethylpropan-1-al (floralozone), 3-(4-tert-butylphenyl)-2-methylpropanal, 3-(3,4-methylenedioxyphenyl)-2-methylpropan-1-al (helional), 3-(4-ethylphenyl)-2,2-dimethylpropanal, 3-(3-isopropylphenyl)butan-1-al (florhydral), 2,6-dimethylhep-5-en-1-al (melonal), n-decanal, n-undecanal, n-dodecanal, 3,7-dimethyl-2,6-octadien-1-al (citral), 4-methoxybenzaldehyde (anisaldehyde), 3-methoxy-4-hydroxybenzaldehyde (vanillin), 3-ethoxy-4-hydroxybenzaldehyde (ethyl vanillin), 3,4-methylenedioxybenzaldehyde (heliotropin), 3,4-dimethoxybenzaldehyde.

Ketal Releasable Components: The ketals of the present invention have two types of releasable components, namely alcohols and ketones. Hydrolysis of a ketal will yield two equivalents of releasable alcohol and one equivalent of releasable ketone. The released ketone, when taken together with the released alcohol, forms a binary fragrance accord. For example di-linalyl β-ionone ketal releases the binary accord linaloolβ-ionone.

When $R^1$ is a moiety as described herein above other than hydrogen, the pro-accords are capable of releasing an ketone component. Preferred ketones which are releasable components of the ketals of the present invention include but are not limited to α-damascone, β-damascone, δ-damascone, β-damascenone, muscone, 6,7-dihydro-1,1,2,3,3-pentamethyl-4(5H)-indanone (cashmeran), cis-jasmone, dihydrojasmone, α-ionone, β-ionone, dihydro-β-ionone, γ-methyl ionone, α-iso-methyl ionone, 4-(3,4-methylenedioxyphenyl)butan-2-one, 4-(4-hydroxyphenyl) butan-2-one, methyl β-naphthyl ketone, methyl cedryl ketone, 6-acetyl-1,1,2,4,4,7-hexamethyltetralin (tonalid), l-carvone, 5-cyclohexadecen-1-one, acetophenone, decatone, 2-[2-(4-methyl-3-cyclohexenyl-1-yl)propyl] cyclopentan-2-one, 2-sec-butylcyclohexanone, β-dihydro ionone, allyl ionone, α-irone, α-cetone, α-irisone, acetanisole, geranyl acetone, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, ethyl amyl ketone, ethyl pentyl ketone, menthone, methyl-7,3-dihydro-2H-1,5-benzodioxepine-3-one, fenchone, and mixtures thereof.

More preferably the ketones which are released by the ketals of the present invention are α-damascone, β-damascone, δ-damascone, β-damascenone, muscone, 6,7-dihydro-1,1,2,3,3-pentamethyl-4(5H)-indanone (cashmeran), cis-jasmone, dihydrojasmone, α-ionone, β-ionone, dihydro-β-ionone, δ-methyl ionone, (α-iso-methyl ionone, 4-(3,4-methylenedioxyphenyl)butan-2-one, 4-(4-hydroxyphenyl)-butan-2-one, methyl β-naphthyl ketone, methyl cedryl ketone, 6-acetyl -1,1,2,4,4,7-hexamethyltetralin (tonalid), l-carvone, 5-cyclohexadecen-1-one, and mixture thereof.

Non-limiting examples of alcohols suitably released by the hydrolysis of the acetal and ketal pro-accords include methanol, 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), 2,4,6-trimethyl-3-cyclohexene-1-methanol (Isocyclo geraniol), 4-(1-methylethyl)cyclohexanemethanol (Mayol), α-3,3-trimethyl-2-norborane methanol, 1,1-dimethyl-1-(4-methylcyclohex-3-enyl)methanol, ethanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)ethanol, 3,3-dimethyl-$\Delta^2$-β-norbornane ethanol, 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methyl-phenyl)ethanol, n-propanol, 2-propanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), (α-n-pentyl-3-phenyl-2-propen-1-ol (α-amyl-cinnamyl alcohol), ethyl-3-hydroxy-3-phenyl propionate, 2-(4-methylphenyl)-2-propanol, n-butanol, 2-butanol, 3-methylbutanol, 3-(4-methylcyclohex-3-ene) butanol, 2-methyl-4-(2,2,3-trimethyl-3-cyclopenten-1-yl) butanol, 2-ethyl-4-(2,2,3-trimethyl-cyclopent-3-enyl)-2-buten-1-ol, 3-methyl-2-buten-1-ol, 2-methyl-4-(2,2,3-trimethyl-3-cyclopenten-1-yl)-2-buten-1-ol, 3-hydroxy-2-butanone, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)butan-2-one, pentanol, cis-3-pentenol, 3-methyl-pentanol, 3-methyl-3-penten-1-ol, 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0(2,6)]hept-3-yl)-2-penten-1-ol (santalol), 4-methyl-1-phenyl-2-pentanol, (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexnol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol, 1-methyl-4-isopropenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol, 4-isopropyl-cyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1,2-dimethyl-3-(1-methylethyl)cyclohexan-1-ol, heptanol, 2,4-dimethylheptan-1-ol, 2,4-dimethyl-2,6-heptandienol, 6,6-dimethyl-2-oxymethylbicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1]heptan -2-ol, 2,6-dimethylheptan-2-ol, 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-1,6-octadien-3-ol (linalool),3,7-dimethyloctan-1ol -(pelagrol), 3,7-dimethyloctan-3-ol (tetrahydrolinalool), 2,4-octadien-1-ol, 3,7-dimethyl-6-octen-3-ol, 2,6-dimethyl-7-octen-2-ol, 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6=-nonadien-3-ol, decanol, 9-decenol, 2benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linallol), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol, 3,7,11,15-tetramethylhexadec-2-en-1-ol (phytol), 3,7,11,15-tetramethylhexadec 1-en-3-ol (iso phytol), benzyl alcohol, p-methoxy benzyl alcohol (anisyl alcohol), para-cymen-7-ol (cuminyl alcohol), 4methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydrozytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro- 2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl) tetrahydrofuran, β-caryophyllene alcohol, and mixtures thereof.

Preferred alcohols which are released by the acetals and ketals of the present invention are 4-(1-methylethyl) cyclohexanemethanol (mayol), 2,4-dimethyl-3-cyclohexen-1-ylmethanol (floralol), 2,4-dimethylcyclohex-1-ylmethanol (dihydrofloralol), 2,4,6-trimethyl-3-cyclohexen-1-ylmethanol (isocyclogeraniol), 2-phenylethanol, 1(4-isopropylcyclohexyl)ethanol (mugetanol), 2-(o-methylphenyl) ethanol (ortho-hawthanol), 2-(m-methylphenyl)ethanol (meta-hawthanol), 2-(p-methylphenyl)ethanol (para-hawthanol), 2,2-dimethyl-3-(3-methylphenyl)propan-1-ol (majantol), 3-phenyl-2-propen-1-ol (cinnamic alcohol), 2-methyl-4-(2,2,3-trimethyl-3-cyclopenten-1-yl)-2-buten-1-ol (santalaire), 3-methyl-5-phenylpentan-1-ol (phenoxanol), 3-methyl-5-(2,2,3-trimethyl-3-cyclopenten-1-yl)-4-penten-2-ol (ebanol), 2-methyl-4-phenylpentan-1-ol (pamplefleur), cis-3-hexen-1-ol, 3,7-dimethyl-6-octen-1-ol (citronellol), 3,7-dimethyl-2,6-octadien-1-ol (geraniol, nerol or mixtures thereof), 7-methoxy-3,7-dimethyloctan-2-ol (osyrol), 6,8-dimethylnonan-2-ol, cis-6-nonen-1-ol, 2,6-nonadien-1-ol, 4-methyl-3-decen-5-ol (undecavertol), benzyl alcohol, 2-methoxy-4-(1-propenyl)phenol (isoeugenol), 2-methoxy-4-(2-propenyl)phenol (eugenol), 4-hydroxy-3-methoxybenzaldehyde (vanillin), and mixtures thereof.

Orthocarbonates

Another class of preferred compounds useful as pro-accords according to the present invention are orthocarbonates having the formula:

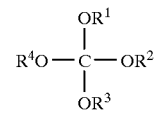

wherein hydrolysis of the orthoester releases the fragrance raw material components according to the following scheme:

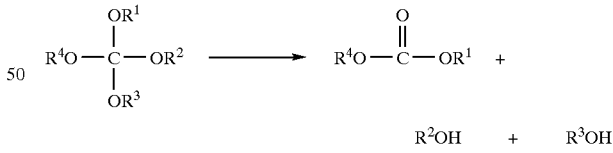

wherein $R^1$, $R^2$, $R^3$, and $R^4$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof. By the term "substituted" herein is meant "compatible moieties which replace a hydrogen atom". Non-limiting examples of substituents are hydroxy, nitro, halogen, nitro, carboxyl (—CHO; —$CO_2H$; —$CO_2R'$; —$CONH_2$;

—CONHR'; —CONR'$_2$; wherein R' is C$_1$–C$_{12}$ linear or branched alkyl), amino, C$_1$–C$_{12}$ mono- and dialkylamino, and mixtures thereof.

In addition to the releasable alcohols listed herein above, orthocarbonates according to the present invention are also cyclic orthocarbonates which are comprised from at least one diol having the formula:

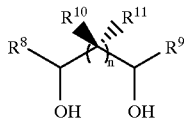

wherein R$^8$, R$^9$, R$^{10}$, and R$_{11}$ are each independently hydrogen, C$_1$–C$_{20}$ linear or branched alkyl, C$_1$–C$_{20}$ linear or branched alkenyl, C$_1$–C$_{20}$ linear, branched or cyclic alkylenecarboxy, C$_1$–C$_{20}$ linear, branched, or cyclic carboxyalkyl, C$_1$–C$_{20}$ linear or branched alkyleneamino, C$_1$–C$_{20}$ linear or branched aminoalkyl, C$_1$–C$_{20}$ linear, branched, or cyclic alkylenecarboxamido, C$_1$–C$_{20}$ linear or branched carboxamidoalkyl, alkyleneoxy having the formula:

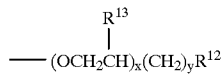

wherein R$^{12}$ is hydrogen or methyl; R$^{13}$ is hydrogen or C$_1$–C$_2$ alkyl; n is from 0 to 4, x is from 1 to about 20, y is from 0 to about 20.

In addition to the initial release of two equivalents of alcohol and one equivalent of carbonate by the scheme depicted herein above, the carbonate pro-fragrances which are released by the orthocarbonates can continue to hydrolyze and further release two equivalents of one or more fragrance raw material alcohol according to the following scheme:

thereby providing up to four equivalents of fragrance raw material alcohol per equivalent of delivered orthocarbonate. The carbonate pro-fragrance which is released by the orthocarbonate may itself be a fragrance raw material in addition to being a pro-fragrance, preferably the carbonate which is released serves as a fragrance raw material. An orthocarbonate which comprises four different fragrance raw materials will always release a carbonate that is a pro-accord (hydrolyzes to release a binary accord) in addition to any further fragrance properties attributable to the carbonate.

Non-limiting examples of R$^1$, R$^2$, R$^3$, and R$^4$ include methyl, 2,4-dimethyl-3-cyclo-hexene-1-methyl (Floralol), 2,4-dimethyl cyclohexane methyl (Dihydro floralol), 5,6-dimethyl-1-methylethenyl-bicyclo[2.2.1]hept-5-ene-2-methyl (Arbozol), 2,4,6-trimethyl-3-cyclohexene-1-methyl (Isocyclo geranyl), 4-(1-methylethyl)cyclohexylmethyl (Mayol), α-3,3-trimethyl-2-norboranylmethyl, 1,1-dimethyl-1-(4-methylcyclohex-3-enyl)methyl, ethyl, 2-phenylethyl, 2-cyclohexylethyl, 2-(o-methylphenyl)ethyl, 2-(m-methylphenyl)ethyl, 2-(p-methylphenyl)ethyl, 6,6-dimethylbicyclo[3.1.1]hept-2-ene-2-ethyl (nopyl), 2-(4-methylphenoxy)ethyl, 3,3-dimethyl-Δ$^2$-β-norboranylmethyl, 2-methyl-2-cyclohexylethyl, 1-(4-isopropylcyclohexyl)ethyl, 1-phenyl-1-hydroxyethyl, 1,1-dimethyl-2-phenylethyl, 1,1-dimethyl-2-(4-methylphenyl) ethyl, propyl, 1-phenylpropyl, 3-phenylpropyl, 2-phenylpropyl (Hydrotropic Alcohol), 2-(cyclododecyl)-propan-1-yl (Hydroxyambran), 2,2-dimethyl-3-(3-methylphenyl)propan-1-yl (Majantol), 2-methyl-3-phenylpropyl, 3-phenyl-2-propen-1-yl (cinnamyl alcohol), 2-methyl-3-phenyl-2-propen-1-yl (methylcinnamyl alcohol), (α-n-pentyl-3-phenyl-2-propen-1-yl (α-amylcinnamyl alcohol), ethyl-3-hydroxy-3-phenyl propionate, 2-(4-methylphenyl)-2-propyl, butyl, 3-methylbutyl, 3-(4-methylcyclohex-3-ene)butyl, 2-methyl-4-(2,2,3-trimethyl-3-cyclopenten-1-yl)butyl, 2-ethyl-4-(2,2,3-trimethylcyclopent-3-enyl)-2-buten-1-yl, 3-methyl-2-buten-1-yl, 2-methyl-4-(2,2,3-trimethyl-3-cyclopenten-1-yl)-2-buten-1-yl, 3-hydroxy-2-butanone, ethyl 3-hydroxybutyrate, 4-phenyl-3-buten-2-yl, 2-methyl-4-phenylbutan-2-yl, 4-(4-hydroxyphenyl)butan-2-one, 4-(4-hydroxy-3-methoxyphenyl)butan-2-one, pentyl, cis-3-pentenyl, 3-methylpentyl, 3-methyl-3-penten-1-yl, 2-methyl-4-phenylpentyl (Pamplefleur), 3-methyl-5-phenylpentyl (Phenoxanyl), 2-methyl-5-phenylpentyl, 2-methyl-5-(2,3-dimethyltricyclo[2.2.1.0(2,6)]hept-3-yl)-2-penten-1-yl (santalyl), 4-methyl-1-phenyl-2-pentyl, (1-methyl-bicyclo[2.1.1]hepten-2-yl)-2-methylpent-1-en-3-yl, 3-methyl-1-phenylpent-3-yl, 1,2-dimethyl-3-(1-methylethenyl)cyclopent-1-yl, 2-isopropyl-4-methyl-2-hexenyl, cis-3-hexen-1-yl, trans-2-hexen-1-yl, 2-isopropenyl-5-methyl-4-hexen-1-yl (Lavandulyl), 2-ethyl-2-prenyl-3-hexenyl (silwanol), 2-ethylhexyl, 1-hydroxymethyl-4-isopropenyl-1-cyclohexenyl (Dihydrocuminyl), 1-methyl-4-isopropenylcyclohex-6-en-2-yl (carvenyl), 6-methyl-3-isopropenylcyclohex-1-yl, 1-methyl-4-isopropenylcyclohex-3-yl, 4-iso-propyl-1-methylcyclohex-3-yl, 4-tert-butylcyclohexyl, 2-tert-butylcyclohexyl, 2-tert-butyl-4-methylcyclohexyl, 4-isopropylcyclohexyl, 4-methyl-1-(1-methylethyl)-3-cyclohexen-1-yl, 2-(5,6,6-trimethyl-2-norbornyl) cyclohexyl, isobornylcyclohexyl, 3,3,5-trimethylcyclohexyl, 1-methyl-4-isopropylcyclohex-3-yl (menthol), 1,2-dimethyl-3-(1-methylethyl) -cyclohexan-1-yl, heptyl, 2,4-dimethylhept-1-yl, 2,4-dimethyl-2,6-heptandienyl, 6,6-dimethyl-2-oxymethylbicyclo[3.1.1]hept-2-en-1-yl (myrtenyl), 4-methyl-2.4-heptadien-1-yl, 3,4,5,6,6-pentamethyl-2-heptyl, 3,6-dimethyl-3-vinyl-5-hepten-2-yl, 6,6-dimethyl-3-hydroxy-2-methylenebicyclo[3.1.1]-heptyl, 1,7,7-trimethylbicyclo[2.2.1]hept-2-yl, 2,6-dimethylhept-2-yl, 2,6,6-trimethylbicyclo[1.3.3]hept-2-yl, octyl, 2-octenyl, 2-methyloctan-2-yl, 2-methyl-6-methylene-7-octen-2-yl (myrcenyl), 7-methyloctan-1-yl, 3,7-dimethyl-6-octenyl, 3,7-dimethyl-7-octenyl, 3,7-dimethyl-6-octen-1-yl (citronellyl), 3,7-dimethyl-2,6-octadien-1-yl (geranyl), 3,7-dimethyl-2,6-octadien-1-yl (neryl), 3,7-dimethyl-1,6-octadien-3-yl (linalyl), 3,7-dimethyloctan-1-yl (pelagryl), 3,7-dimethyloctan-3-yl (tetrahydrolinalyl), 2,4-octadien-1-yl, 3,7-dimethyl-6-octen-3-yl, 2,6-dimethyl-7-octen-2-yl, 2,6-dimethyl-5,7-octadien-2-yl, 4,7-dimethyl-4-vinyl-6-octen-3-yl, 3-methyloctan-3-yl, 2,6-dimethyloctan-2-yl, 2,6-dimethyloctan-3-yl, 3,6- dimethyloctan-3-yl, 2,6-dimethyl-7-octen-2-yl, 2,6-dimethyl-3,5-octadien-2-yl (mugyl), 3-methyl-1-octen-3-yl, 7-hydroxy-3,7-dimethyloctanalyl, 3-nonyl, 6,8-dimethylnonan-2-yl, 3-(hydroxymethyl)-2-nonanone, 2-nonen-1-yl, 2,4-nonadien-1-yl, 2,6-nonadien-1-yl, cis-6-nonen-1-yl, 3,7-dimethyl-1,6-nonadien-3-yl, decyl, 9-decenyl, 2-benzyl-M-dioxa -5-yl, 2-decen-1-yl, 2,4-decadien-1-yl, 4-methyl-3-decen-5-yl, 3,7,9-trimethyl-1,6-decadien-3-yl (isobutyl linallyl), undecyl, 2-undecen-1-yl, 10-undecen-1-yl, 2-dodecen-1-yl, 2,4-dodecadien-1-yl, 2,7,11-trimethyl-2,6,10-dodecatrien-1-yl (farnesyl), 3,7,11-trimethyl-1,6,10,-dodecatrien-3-yl, 3,7,11,15-tetramethylhexadec-2-en-1-yl (phytyl), 3,7,11,15-tetramethylhexadec-1-en-3-yl (iso phytol), benzyl, p-methoxybenzyl (anisyl), para-cymen-7-yl (cuminyl), 4-methylbenzyl, 3,4-methylenedioxybenzyl, 2-(methyl) carboxy-1-hydroxyphenyl, 2-(benzyl)carboxy-1-hydroxyphenyl, 2-(cis-3-hexenyl)-carboxy-1-hydroxyphenyl, 2-(n-pentyl)carboxy-1-hydroxyphenyl, 2-(2-phenylethyl)carboxy-1-hydroxyphenyl, 2-(n-hexyl) carboxy-1-hydroxyphenyl, 2-methyl-5-isopropyl-1-hydroxyphenyl, 4-ethyl-2-methoxyphenyl, 4-allyl-2-methoxy-1-hydroxyphenyl (eugenyl), 2-methoxy-4-(1-propenyl)-1-hydroxyphenyl (isoeugenyl), 4-allyl-2,6-dimethoxy-1-hydroxyphenyl, 4-tert-butyl-1-hydroxyphenyl, 2-ethoxy-4-methyl-1-hydroxyphenyl, 2-methyl-4-vinyl-1-hydroxyphenyl, 2-isopropyl-5-methyl-1-hydroxyphenyl (thymyl), 2-(isopentyl)carboxy-1-hydroxyphenyl, 2-(ethyl) carboxy-1-hydroxyphenyl, 6-(methyl)carboxy-2,5-dimethyl-1,3-dihydroxyphenyl 5-methoxy-3-methyl-1-hydroxyphenyl, 2-tert-butyl-4-methyl-1-hydroxyphenyl, 1-ethoxy-2-hydroxy-4-propenylphenyl, 4-methyl-1-hydroxyphenyl, 4-hydroxy-3-methoxybenzaldehyde, 2-ethoxy-4 -hydroxybenzaldehyde, decahydro-2-naphthyl, 2,5,5-trimethyl-octahydro-2-naphthyl, 1,3,3-trimethyl-2-norbornyl (fenchyl), 3a,4,5,6,7,7a-hexahydro-2,4-dimethyl-4,7-methano-1H-inden-5-yl, 3a,4,5,6,7,7a-hexahydro-3,4-dimethyl-4,7-methano-1H-inden-5-yl, 2-methyl-2-vinyl-5-(1-hydroxy-1-methylethyl)tetrahydrofuranyl, β-caryophyllenyl, and mixtures thereof.

Orthocarbonate Releasable Components: The initial hydrolysis of the orthocarbonates of the present invention release two types of components, alcohols and carbonates. As indicated herein above, the carbonates can further break down to release further alcohols. The first hydrolysis of an orthocarbonate pro-accord releases two equivalents of alcohol and one equivalent of carbonate. The released carbonate, when taken together with the released alcohol, forms a binary fragrance accord. For example tetra-geranyl orthocarbonate releases the binary accord geraniol/di-geranyl carbonate. Non-limiting examples of alcohols suitably released by the hydrolysis of the orthocarbonate pro-accords include methanol, 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), 2,4,6-trimethyl-3-cyclohexene-1-methanol (Isocyclo geraniol), 4-(1-methylethyl)cyclohexanemethanol (Mayol), α-3,3-trimethyl-2-norborane methanol, 1,1-dimethyl-1-(4-methylcyclohex-3-enyl)methanol, ethanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)ethanol, 3,3-dimethyl-Δ2-β-norbornane ethanol, 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, n-propanol, 2-propanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, n-butanol, 2-butanol, 3-methylbutanol, 3-(4-methylcyclohex-3-ene) butanol, 2-methyl-4-(2,2,3-trimethyl- 3-cyclopenten-1-yl) butanol, 2-ethyl-4-(2,2,3-trimethyl-cyclopent-3-enyl)-2-buten-1-ol, 3-methyl-2-buten-1-ol, 2-methyl-4-(2,2,3-trimethyl-3-cyclopenten-1-yl)-2-buten-1-ol, 3-hydroxy-2-butanone, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)butan-2-one, pentanol, cis-3-pentenol, 3-methyl-pentanol, 3-methyl-3-penten-1-ol, 2-methyl-4-phenylpentanol (Pamplefleur), 3-methyl-5phenylpentanol (Phenoxanol), 2-methyl-5-phenylpentanol, 2-methyl-5-(2,3-dimethyltricyclo[2.2.1.0(2,6)]hept-3-yl)-2-penten-1-ol (santalol), 4-methyl-1-phenyl-2-pentanol, (1-methyl-bicyclo[2.1.1]hepten-2-yl)-2-methylpent-1-en-3-ol, 3-methyl-1-phenylpentan-3-ol, 1,2-dimethyl-3-(1methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol, 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol, 4-isopropyl-cyclohexanol, 4-methyl-1-(1methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1,2-dimethyl-3-(1methylethyl)cyclohexan-1-ol, heptanol, 2,4-dimethylheptan-1-ol, 2,4-dimethyl-2,6-heptandienol, 6,6-dimethyl-2-oxymethylbicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1]heptan-2-ol, 2,6-dimethylheptan-2-ol, 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-1,6-octadien-3-ol (linalool), 3,7-dimethyloctan-1-ol (pelagrol), 3,7-dimethyloctan-3-ol (tetrahydrolinalool), 2,4-octadien-1-ol, 3,7-dimethyl-6-octen-3-ol, 2,6-dimethyl-7-octen-2-ol, 2,6-dimethyl-5,7-octadien-2-ol, 4,7-dimethyl-4-vinyl-6- octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linallol), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol, 3,7,11,15-tetramethylhexadec-2-en-1-ol (phytol), 3,7,11,15-tetramethylhexadec 1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl -2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydrozytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl) tetrahydrofuran, β-caryophyllene alcohol, and mixtures thereof.

Preferred alcohols released by the orthocarbonate pro-accords of the present invention are 4-(1-methylethyl) cyclohexanemethanol (mayol), 2,4-dimethyl-3-cyclohexen-1-ylmethanol (floralol), 2,4-dimethylcyclohex-1-ylmethanol (dihydrofloralol), 2,4,6-trimethyl-3-cyclohexen-1-ylmethanol (isocyclogeraniol), 2-phenylethanol, 1-(4-isopropylcyclohexyl)ethanol (mugetanol), 2-(o-methylphenyl)ethanol (ortho-hawthanol), 2-(m-methylphenyl)ethanol (meta-hawthanol), 2-(p-methylphenyl)ethanol (para-hawthanol), 2,2-dimethyl-3-(3-methylphenyl)propan-1-ol (majantol), 3-phenyl-2-propen-1-ol (cinnamic alcohol), 2-methyl-4-(2,2,3-trimethyl-3-cyclopenten-1-yl)-2-buten-1-ol (santalaire), 3-methyl-5-phenylpentan-1-ol (phenoxanol), 3-methyl-5-(2,2,3-trimethyl-3-cyclopenten-1-yl)-4-penten-2-ol (ebanol), 2-methyl-4-phenylpentan-1-ol (pamplefleur), cis-3-hexen-1-ol, 3,7-dimethyl-6-octen-1-ol (citronellol), 3,7-dimethyl-2,6-octadien-1-ol (geraniol, nerol or mixtures thereof), 7-methoxy-3,7-dimethyloctan-2-ol (osyrol), 6,8-dimethylnonan-2-ol, cis-6-nonen-1-ol, 2,6-nonadien-1-ol, 4-methyl-3-decen-5-ol (undecavertol), benzyl alcohol, 2-methoxy-4-(1-propenyl)phenol (isoeugenol), 2-methoxy-4-(2-propenyl)phenol (eugenol), 4-hydroxy-3-methoxybenzaldehyde (vanillin), and mixtures thereof.

Non-limiting examples of preferred orthocarbonate pro-accords according to the present invention include: bis (ethyl) bis(geranyl)orthocarbonate, bis(ethyl) bis (phenylethyl)orthocarbonate, bis(ethyl) bis(cis-3-hexenyl) orthocarbonate, bis(ethyl) bis(citronellyl)orthocarbonate, bis(ethyl) bis(linalyl)orthocarbonate, bis(ethyl) bis (menthyl)orthocarbonate, bis(dodecyl) bis(geranyl) orthocarbonate, and bis(dodecyl) bis(phenylethyl) orthocarbonate.

The more preferred orthocarbonate pro-accords of the present invention comprise at least three of the $R^1$, $R^2$, $R^3$, and $R^4$ moieties which are derived from a fragrance raw material alcohol, thereby the preferred pro-fragrances have a molecular weight which is at least 3 times the molecular weight of the lowest "fragrance raw material alcohol" which comprises the orthocarbonate pro-fragrance. Further, the more preferred orthocarbonate pro-fragrances have a molecular weight which is greater than or equal to 325 g/mol.

Non-limiting examples of more preferred orthocarbonate pro-accords according to the present invention include: methyl tris(geranyl)orthocarbonate, ethyl tris(geranyl) orthocarbonate, methyl tris(phenylethyl)orthocarbonate, ethyl tris(phenylethyl)orthocarbonate, methyl tris(cis-3-hexenyl)orthocarbonate, ethyl tris(cis-3-hexenyl) orthocarbonate, methyl tris(citronellyl)orthocarbonate, ethyl tris(citronellyl)orthocarbonate, methyl tris(linalyl) orthocarbonate, ethyl tris(linalyl) orthocarbonate, methyl tris(menthyl)orthocarbonate, ethyl tris(menthyl) orthocarbonate, dodecyl tris(geranyl)orthocarbonate, and dodecyl tris(phenylethyl) orthocarbonate.

The most preferred orthocarbonate pro-accords of the present invention have each of the $R^1$, $R^2$, $R^3$, and $R^4$ moieties derived from a fragrance raw material alcohol, thereby the preferred pro-fragrances have a molecular weight which is at least 4 times the molecular weight of the lowest "fragrance raw material alcohol" which comprises the orthocarbonate pro-accord. Further, the preferred orthocarbonate pro-accords have a molecular weight which is greater than or equal to 350 g/mol.

Non-limiting examples of most preferred orthocarbonate pro-accords according to the present invention include: tetra-geranyl orthocarbonate, tetra phenylethyl orthocarbonate, tetrakis(3-methyl-5-phenylpentyl) orthocarbonate, tetrakis(cis-3-hexenyl)orthocarbonate, bis (geranyl) bis(cis-3-hexenyl) orthocarbonate, bis (phenylethyl) bis(cis-3-hexenyl)orthocarbonate, tetrakis (citronellyl)orthocarbonate, tetrakis(linalyl)orthocarbonate, bis(linallyl) bis(geranyl)orthocarbonate, tetrakis(myrcenyl) orthocarbonate, tetrakis(cinnamyl) orthocarbonate.

Fragrance Release Half-life

The pro-accords useful in the perfume and fine fragrance compositions of the present invention generally have a delayed release of final fragrance accord in order to achieve the increased fragrance longevity benefits described herein. However, the pro-accords generally also deliver the fragrance accords during a time period useful to the formulator, for example, within a time period desirable to the consumer.

For the purposes of the present invention the pro-accords generally have a "Fragrance Release Half-life" of less than or equal to 12 hours when measured in $NaH_2PO_4$ buffer at pH 2.5 and greater than or equal to 0.1 hour when measured in $NaH_2PO_4$ buffer at pH 5.3. The "Fragrance Release Half-life" is defined herein as follows.

Pro-accords deliver their corresponding mixture of fragrance raw materials or fragrance accords according to the equation:

$$\text{Pro-Accord} \rightarrow \text{Accord}$$

wherein the accord which is released may be a binary accord or a multiple fragrance raw material accord.

The rate at which the accord is released is defined by the formula:

$$\text{Rate} = k[\text{Pro-accord}]$$

and can be further expressed by the formula:

$$-\frac{d[\text{Pro-accord}]}{dt} = k[\text{Pro-accord}]$$

wherein k is the release rate constant and [Pro-accord] is the concentration of pro-accord. For the purposes of the present invention the "Fragrance Release Half-life", $t_{1/2}$ is related to the release rate constant by the formula:

$$t_{1/2} = \frac{0.693}{k}$$

and this relationship is used for the purposes of the present invention to determine the "fragrance Release Half-life" (FRHL).

An example of the procedure used to measure the suitability of a pro-accord for use in the fragrance delivery systems at pH 2.5 is as follows. The phosphate buffered water is prepared by admixing 3.95 mL of 85% phosphoric acid ($H_3PO_4$) and 24 g of sodium dihydrogen phosphate ($NaH_2PO_4$) with one liter of water. The pH of this solution is approximately 2.5. Next 10 mL of the phosphate buffer is admixed with 90 mL of dioxane and the pro-fragrance to be analyzed is added. The hydrolysis kinetics are then monitored by conventional HPLC at 30° C.

Table 1 lists several pro-accords according to the present invention with their corresponding $t_{1/2}$ values.

TABLE I

| Pro-accord | $t_{1/2}$* |
|---|---|
| tris(phenylethyl) orthoformate | 5.9 |
| tetrakis(phenylethyl) orthocarbonate | 4.8 |

*$t_{1/2}$ for the purposes of the present invention is measured in hours.

As indicated in the table above tris(phenylethyl) orthoformate is suitable for use as a pro-fragrance for delivering a "rose-floral" character note to an accord having enhance longevity. In some instances, it is desirable to formulate pro-accords having one or more pro-fragrances which deliver a rapid release of fragrance raw material in addition to the delayed onset of a fragrance. In such cases the hydrolysis rate, and therefore the determination of $t_{1/2}$ must be measured in a buffer system which can accommodate this more rapid hydrolysis rate. For example, the pro-fragrance tris-(phenylethyl)orthoacetate is used to deliver a rapid onset of a "rose-floral" middle note by releasing the fragrance raw material phenylethyl alcohol. The relative release rate of this pro-accord can be suitably determined by substituting a phosphate buffer comprising 4.6 g of sodium dihydrogen phosphate ($NaH_2PO_4$) and 7.9 g of disodium hydrogen phosphate ($Na_2HPO_4$) admixed with 1 liter of water for the phosphate buffer described herein above, then 10 mL of this solution is added to 90 mL of dioxane. Alternatively, the phosphate buffered water is prepared by admixing 3.95 mL of 85% phosphoric acid ($H_3PO_4$) and 24 g of sodium dihydrogen phosphate ($NaH_2PO4$) with one liter of water. The pH of this solution is approximately 2.5. Next 10 mL of the phosphate buffer is admixed with 90 mL of dioxane and the pro-fragrance to be analyzed is added.

Therefore, by admixing sufficient quantities of tris (phenylethyl) orthoformate and tris(phenylethyl) orthoacetate into a pro-accord the formulator can achieve a rapid as well as delayed onset of the "rose-floral" character note provided by the perfume raw material phenylethyl alcohol.

Odor Value

The pro-accords of the present invention typically have an Odor Value greater than or equal to about 1, preferably greater than or equal to about 5, more preferably greater than or equal to about 10. The term "Odor Value" is defined by the following formula:

$$OV = \frac{[\text{Concentration of } FRM]}{ODT}$$

wherein OV is the odor value of the fragrance raw material released upon the skin by the pro-accord. The odor value is the concentration of the fragrance raw material, FRM, on the skin surface divided by the Odor Detection Threshold, ODT. The term "level of noticeability" is often applied to and substituted for the term "odor value".

Odor Detection Threshold

For the purposes of the present invention the term "odor detection threshold" is defined as the level at which a fragrance raw material is perceptible to the average human. The odor detection threshold (ODT) of the compositions of the present invention are preferably measured by carefully controlled gas chromatograph (GC) conditions as described hereinbelow. The preferred fragrance raw materials of the present invention have an ODT of at least about 100 part per billion (ppb), more preferably 10 ppb, most preferably 1 ppb. Fragrance raw materials having an ODT greater than 10 parts per million (ppm) are typically avoided unless useful as an adjunct ingredient, for example, as an adjunct alcohol when adjusting the fragrance release half-life of an orthoester.

Determination of Odor Detection Thresholds is as follows. A gas chromatograph is characterized to determine the exact volume of material injected by a syringe, the precise split ratio, and the hydrocarbon response using a hydrocarbon standard of known concentration and chain-length distribution. The air flow rate in accurately measured and, assuming the duration of a human inhalation to last 0.02 minutes, the sampled volume is calculated. Since the precise concentration at the detector at any point in time is known, the mass per volume inhaled is known and hence the concentration of material. To determine whether a material has a threshold below 10 ppb, solutions are delivered to the sniff port at the back-calculated concentration. A panelist sniffs the GC effluent and identities the retention time when odor is notice. The average over all panelists determines the threshold of noticeability or ODT. The necessary amount of analyte is injected onto the column to achieve a 10 ppb concentration at the detector. Typical gas chromatograph parameters for determining odor detection thresholds are listed below.

GC: 5890 Series II with FID detector 7673 Autosampler
Column: J&W Scientific DB-1, length 30 m, i.d. 0.25 mm, film thickness 1 μm.
Split Injection: 17/1 split ratio
Autosampler: 1.13 μl/injection
Column flow: 1.10 mL/min
Air flow: 345 mL/min
Inlet temperature: 245° C.
Detector temperature: 285° C.
Temperature Information:
  Initial temperature: 50° C.
  Rate: 5° C./min
  Final temperature: 280° C.
  Final time: 6 min
Leading assumptions: 0.02 minutes per sniff and that GC air adds to sample dilution.

Symmetrical Pro-accords

Symmetrical pro-accords release the same fragrance raw materials regardless of hydrolysis pathway. An example of a symmetrical pro-accord is tris(phenylethyl) orthoacetate which releases a binary accord having a "rose" characteristic comprising 2 parts phenylethyl alcohol and 1 part phenylethyl acetate according to the following scheme:

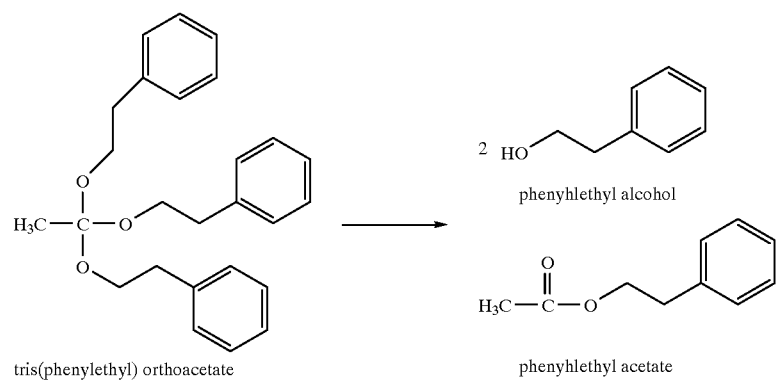

tris(phenylethyl) orthoacetate → phenyhlethyl alcohol + phenyhlethyl acetate

The phenylethyl alcohol/phenylethyl acetate (2:1) simple accord is useful in delivering to fabric a rose or rose/floral characteristic. These are the only fragrance raw materials which are releasable by the pro-accord regardless of hydrolysis pathway.

Unsymmetrical Pro-accords

Unsymmetrical pro-accords have the capacity to release fragrance accords more complex than the binary fragrance accords released by symmetrical pro-accords. The composition of the released accord depends on the route of pro-accord hydrolysis. An unsymmetrical pro-accord can be designed by the formulator to release different ratios of fragrance raw materials based not only on the composition of the pro-accord but on the reactivity as well. In addition, unsymmetrical pro-accords can also be used to produce "adjunct pro-accords" useful for releasing low molecular weight modifiers or astringents in addition to fragrance raw materials.

An example of an unsymmetrical pro-accord is di-citronellyl benzyl acetate capable of releasing the binary fragrance accord of citronellol/citronellyl acetate having a "rose" characteristic together with the benzyl alcohol/benzyl acetate "jasmin" modifiers according to the following scheme:

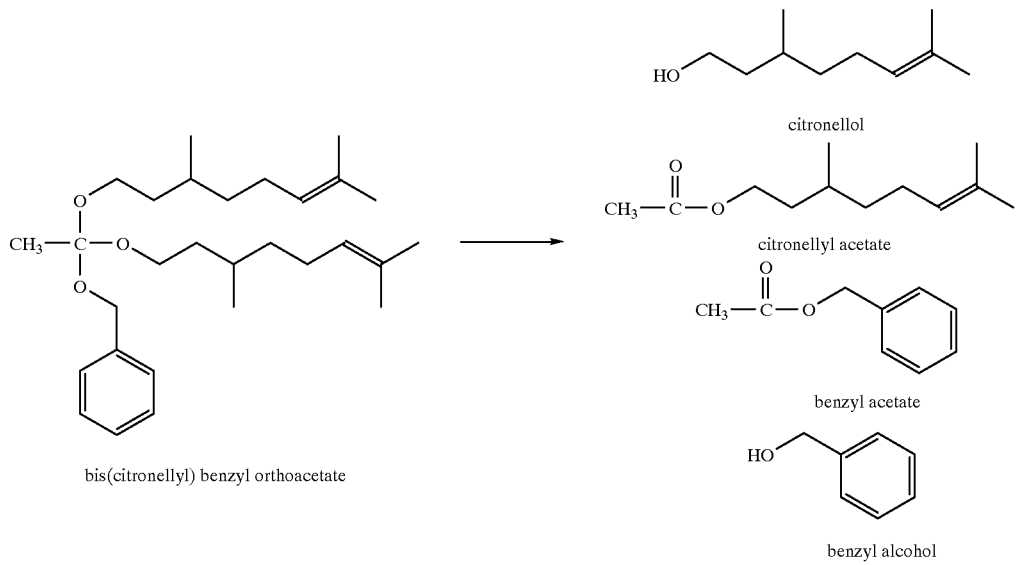

bis(citronellyl) benzyl orthoacetate citronellol citronellyl acetate benzyl acetate benzyl alcohol The above accord can be suitably modified by the formulator to adjust the relative proportions of the accord ingredients. For example, more of the "sweet" diluent benzyl alcohol can be delivered by adjusting the proportion of citronellol and benzyl alcohol used in the pro-accord. Di-benzyl citronellyl orthoacetate delivers the same fragrance raw materials as di-citronellyl benzyl orthoacetate, only the relative amounts of the released materials differ.

As described herein above, a principle aspect of the present invention is the ability of certain pro-accords to deliver more than one fragrance raw material when the "pro-accord" has been formed from only one fragrance raw material. These pro-accords, which preferably include the formate, acetate, propionate, benzoate, and phenylacetate orthoesters of fragrance raw material alcohols can be summarized as:

a) said pro-accord is formed from n number of fragrance raw materials;
b) said pro-accord contains n number of fragrance raw materials in a releasable form; and
c) said pro-accord when releasing the fragrance raw materials releases at least n+1 fragrance raw materials.

According to the present invention all isomers of a fragrance raw material whether in the form of the pro-accord or the released fragrance raw material, are suitable for use in the present invention. When optical isomers are possible fragrance raw materials may be included as either the separate chemical isomer or as the combined racemic mixture. For example, 3,7-dimethyl-6-octen-1-ol, commonly known by those of ordinary skill in the art as β-citronellol or cephrol, comprises a pair of optical isomers, R-(+)-β-citronellol and S-(−)-β-citronellol. Each of these materials separately or as a racemic pair are suitable for use as fragrance raw materials in the present invention. However, those skilled in the art of fragrances, by utilization of the present invention, should not disregard the olfactory differences that individual optical isomers impart. By way of example, carvone, 2-methyl-5-(1-methylethenyl)-2-cyclohexene-1-one exists as two isomers; d-carvone and l-carvone. d-Carvone is found in oil of caraway and renders a completely different fragrance from l-carvone which is found in spearmint oil. According to the present invention a pro-accord which releases d-carvone will result in a different accord than one which releases l-carvone. The same applies to l-carvone.

The pro-accords of the present invention are acetals, ketals, orthoesters, and orthocarbonates which are formed from fragrance raw materials that are selected from the group consisting of primary, secondary, and tertiary alcohols, preferably primary and secondary alcohols, aldehydes, ketones, esters, and mixtures thereof. The pro-accords of the present invention release the fragrance raw materials upon contact with skin or hair, an acid forming, or an acid containing medium.

Human skin exhibits a "buffer capacity" which vigorously maintains a constant pH value. This buffer capacity is referred to as "the acid mantle". Human skin acts rapidly to neutralize acidic or alkaline insults outside this constant pH value. Utilizing this recognition of the "buffer capacity" of the skin, the pro-accords of the present invention which are labile to acid media, can be applied to skin and the acidic nature of said skin can then be effectively used as the acid catalyst to release the parent fragrance raw materials. Therefore, the pro-accords of the present invention which are acid labile generally retain their chemical form at alkaline pH's, preferably at pH greater than 8. What is meant by the term "pro-accords must maintain their chemical form" is that a pro-accord which is in an acid labile form inter alia acetal, ketal, orthoester, or orthocarbonate will not hydrolyze and release the fragrance raw materials at an alkaline pH.

The pro-accord component of the present invention, as described herein above, must have a reserve alkalinity equivalent to at least 0.001 molar (1 millimolar) sodium hydroxide. This generally serves to prevent premature release of the fragrance raw materials which comprise acid labile pro-accords prior to exposure of the pro-accords to skin. For the purposes of the present invention the term "a reserve alkalinity of at least 0.001 molar" is defined as "the amount of alkaline material present in one liter of the first fragrance oil component that is placed in an equivalent volume of water, would produce a hydroxide ion equivalent of 0.001 moles or greater". By way of illustration, 0.0004 g of NaOH present in a 10 mL aliquot of the first fragrance oil component would produce a reserve alkalinity of at least 0.001 molar.

Suitable sources of alkalinity are the alkali metal and alkali earth hydroxides. For example, sodium hydroxide, potassium hydroxide, lithium hydroxide, calcium hydroxide, magnesium hydroxide, sodium carbonate, potassium carbonate, and sodium silicate. However, other suitable sources of alkalinity can be used which are compatible with the pro-accords of the "pro-accord component".

The "fragrance raw material component" of the compositions of the present invention may contain top and middle note as well as base note fragrances. The top and middle notes which comprise this component may be the same or different notes which are released by the pro-accords which comprise the "pro-accord component".

In addition, carriers, fixatives, and other adjunct ingredients may be added to the pro-accord component and the fragrance raw material component. Typical carriers are methanol, ethanol (preferred), iso-propanol, polyethylene glycol, as well as water in some instances, especially as a vehicle to deliver materials which provide reserve alkalinity to the pro-accord component. Fixatives serve to lower the volatility of certain top and middle notes in order to extend their contact time on skin. Adjunct ingredients include perfume raw material components which are essential oils and are therefore not a single chemical entity. In addition, the adjunct ingredients may be mixtures of synthetic fragrance raw materials which serve a purpose in addition to providing a pleasurable odor.

The following are non-limiting examples which illustrate the types of accords which are releasable by the pro-fragrances of the present invention. The examples listed herein below are suitably stabilized under the alkaline conditions described herein above.

The following is an example of the release of the binary accord geraniol/geranyl formate by the pro-accord tris (geranyl)orthoformate:

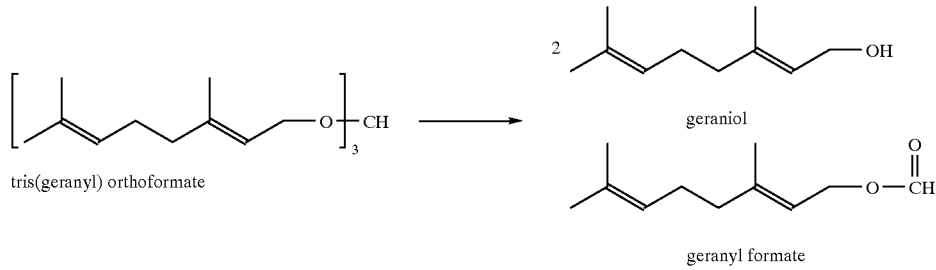

The following is an example of the release of the binary accord citronellol/citronellyl propionate by the pro-accord tris(citronellyl)orthopropionate:

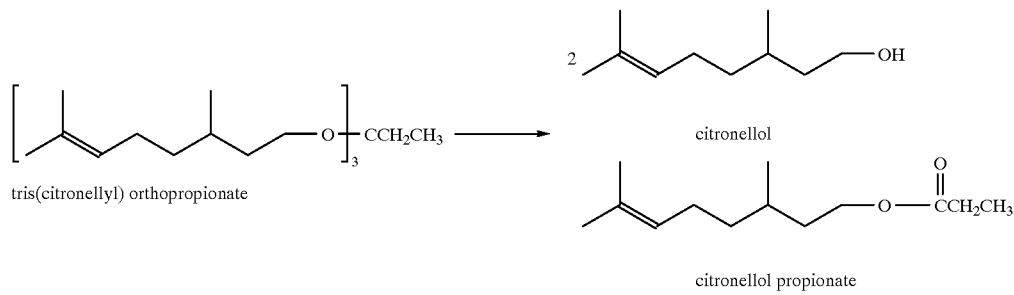

The following is an example of the release of the binary accord cis-6-nonenol/cis-6-nonenyl acetate by the pro-accord tris(cis-6-nonenyl)orthoacetate:

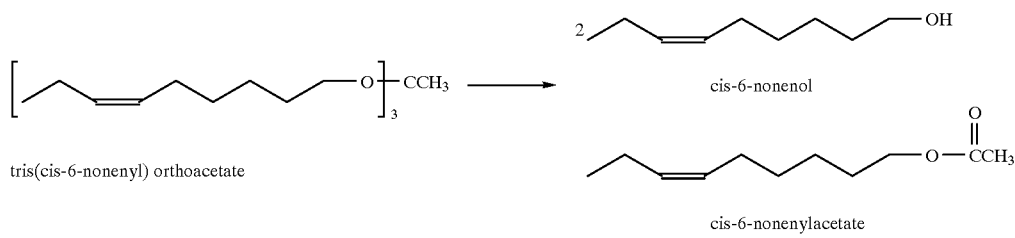

tris(cis-6-nonenyl) orthoacetate → cis-6-nonenol cis-6-nonenylacetate

The following is an example of the release of the binary accord phenylethyl alcohol/phenylethyl benzoate, which comprises a base note, by the pro-accord tris(phenylethyl) orthobenzoate:

The following is an example of the release of the binary accord modifiers benzyl alcohol/benzyl salicylate by the pro-accord tris(benzyl)orthosalicyclate:

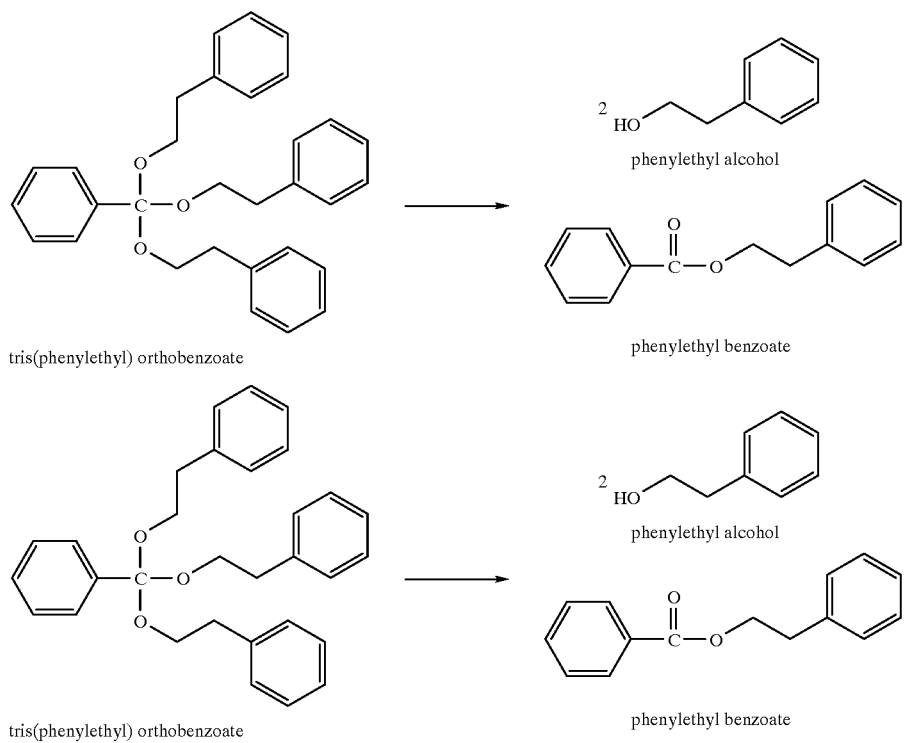

tris(phenylethyl) orthobenzoate → phenylethyl alcohol phenylethyl benzoate tris(phenylethyl) orthobenzoate → phenylethyl alcohol phenylethyl benzoate

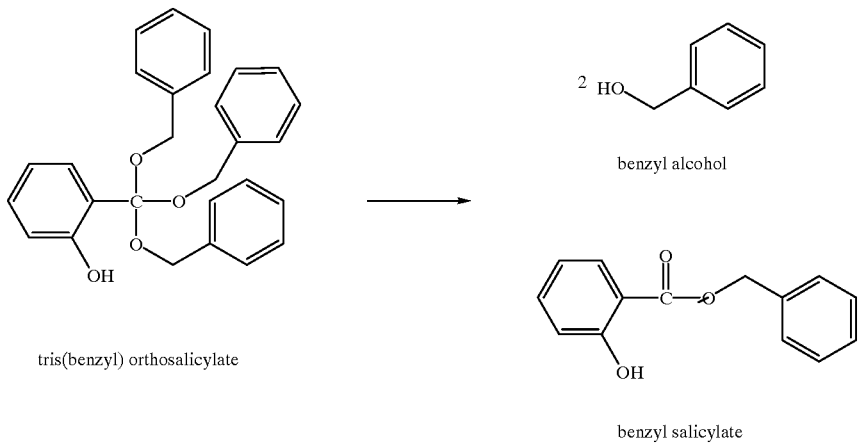

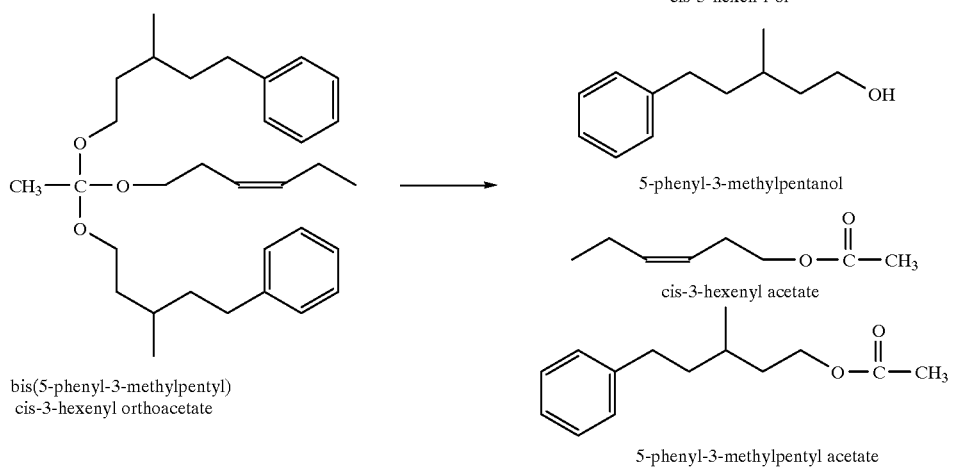

The following is an example of the release of the fragrance accord which comprises cis-3-hexenol, cis-3-hexenyl acetate, 5-phenyl-3-methylpentanol and 5-phenyl3-methylpentyl acetate by the pro-accord bis(5-phenyl-3-methylpentyl)cis-3-hexenyl orthoacetate:

Non-preferred orthoesters which are encompassed within the definition of "orthoesters" hereinabove are orthoesters comprising R units which are hydrogen (formate), methyl (acetate), phenyl (benzoate), benzyl (phenylacetate), phenethyl (phenylpropionate), phenylpropyl (phenylbutyrate), cis-3-hexenyl, or santalyl (α or β) when $R^1$, $R^2$, and $R^3$ comprise only the alcohols selected from group consisting of methanol, phenylethanol, phenylpropanol, cinnamyl alcohol, benzyl alcohol, geraniol, citronellol, α-santalol, β-santalol, and cis-3-hexenol. Especially non-preferred pro-accords are those wherein two $R^1$, $R^2$, or $R^3$ units are methanol which is not a fragrance raw material alcohol. For example, dimethyl geranyl orthoformate, typically releases two equivalents of methanol and one equivalent of geranyl formate. The formulator will recognize that methanol has no intrinsic fragrance value, that an excess of the pro-perfume will need to be released to provide the an odor benefit, and that the pro-perfume itself may be too volatile in some applications and therefore, will evaporate prior to release of the constituent ingredients. However, if these alcohols are combined with an alcohol not of this group, for example, nerol, osyrol, Mayol, these alcohols are suitable as components of a preferred pro-accord.

Changing Fragrance Characteristic

The present invention is also directed to a method which uses the selective release of fragrances to alter or modify the fragrance or scent "characteristic" over the usage time. For example, a perfume, cologne, eau de toilette, after-shave, or other fragrance-containing composition may have an initial smell that is characterized as "raspberry". This composition will typically comprise many components that are middle and base notes and therefore may remain constant. However, the several component fragrance raw materials responsible for the "raspberry" notes may be allowed to diffuse and evaporate while the first fragrance oil component comprises pro-fragrances that release "lilac" notes. After a period of time, the necessary middle and base notes are present but the volatile "raspberry notes" are replaced by "lilac notes" that have been released from pro-fragrances.

An example of a preferred embodiment of the present invention comprises:

a) a first component comprising:
  i) from about 0.1% to about 50% by weight, one or more fragrance raw materials;
  ii) the balance carriers and adjunct ingredients;
b) a second component comprising:
  i) from about 0.5% to about 5% by weight, of nonadyl orthoformate;
  ii) from about 1.5% to about 5% by weight, of mugetanol orthoformate;
  iii) from about 1.5% to about 5% by weight, of osyrol orthoformate;
  iv) from about 1% to about 10% by weight, of one or more pro-accord orthoesters having the formula:

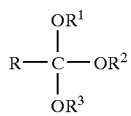

wherein R is hydrogen, $C_1$–$C_8$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof, $R^1$, $R^2$ and $R^3$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl, and mixtures thereof; and
  v) the balance carriers and adjunct ingredients.

The second component of this example of a preferred embodiment of the fragrance delivery systems of the present invention comprises the following pro-accords.

Nonadyl orthoformate. This example of a preferred embodiment of the present invention comprises from about 0.5% to about 5% by weight, of nonadyl orthoformate having the formula:

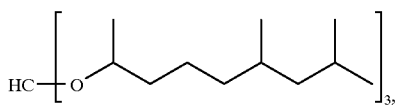

preferably the compositions comprise 0.8% to about 1.6% by weight, of nonadyl orthoformate.

Mugetanol orthoformate. This example of a preferred embodiment of the present invention comprises from about 1.5% to about 5% by weight, of mugetanol orthoformate having the formula:

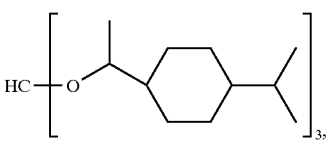

preferably the compositions comprise from about 2.1% to about 4.2% by weight, of mugetanol orthoformate.

Osyrol orthoformate. This example of a preferred embodiment of the present invention comprises from about 1.5% to about 5% by weight, of osyrol orthoformate having the formula:

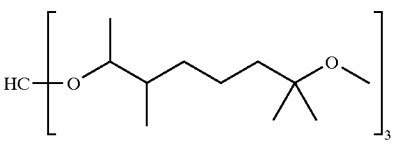

preferably the compositions comprise from about 2.3% to about 4.6% by weight, of osyrol orthoformate.

Orthoesters

This example of a preferred embodiment of the present invention also comprises from about 1% to about 10% by weight, of one or more orthoester pro-accords wherein preferably R is hydrogen, methyl, ethyl, propyl, phenyl, benzyl, and mixtures thereof.

Examples of suitable alcohols and esters released by the preferred pro-accords of the present invention are described hereinabove. An example of a preferred orthoester for use in the fragrance delivery systems of the present invention is benzyl orthoacetate.

Article of Manufacture for Dispensing a Pro-accord Containing Perfume

The present invention further relates to an article of manufacture for dispensing a perfume or fine fragrance which comprises a first reservoir for the pro-accords described herein above. In addition to the pro-accords, the reservoir, container, pouch or chamber may contain carriers, stabilizers, and other adjunct material suitable for use in perfumes, fine fragrances, colognes, eau de toilettes, aftershave lotions and the like. Generally, one or more of the pro-accords may be susceptible to acid catalyzed hydrolysis and therefore to protect from premature release of the fragrance raw materials the pro-accord reservoir contains sufficient basic material to provide an amount of reserve alkalinity equal to at least 0.001 molar NaOH.

The article of manufacture for delivering the pro-accord containing fragrance materials of the present invention has a second reservoir which contains any base note fragrance raw materials or those top and middle note fragrance raw materials which are not suitable for exposure to the alkaline environment which is found in some embodiments of the pro-accord reservoir. In addition, the second reservoir may contain carriers, fixatives, and other adjunct ingredients suitable for use in the fragrance-containing compositions described herein above.

In addition to the first reservoir containing the pro-accord material and the second reservoir containing the balance of the perfume ingredients, the article of manufacture comprises a mixing chamber, mixing tube, delivery tube or other modification which provides for efficient admixing of the material from each reservoir prior to delivering the fragrance material to human skin. The contents may be delivered via squeezing the contents onto the skin wherein the user admixes the contents of the two reservoirs as the materials is worked into the skin. This admixing can be accomplished by means of an "actuating device" wherein the admixture is formed by squeezing a "triggering" device which delivers measured amounts of each reservoir directly to the skin. Alternatively, a mixing chamber or a means for mixing the two components may be incorporated into the article of manufacture. Embodiments which have a "single use" amount of the fragrance material may have a collapsible membrane which separates the contents of the first reservoir from the second reservoir. For example, the user may squeeze a perfume containing pouch and admix the contents by working a flexible container with the fingers prior to opening and application to the skin.

A further embodiment of the article of manufacture of the present invention encompasses a reservoir, container chamber or the like which holds the pro-accord component, said reservoir having an alkaline surface. This embodiment also includes surfaces which are typically a source of acid but which are modified to overcome or remove the acid source. An example of a surface which has been modified includes a glass surface wherein the surface silanols are capped with a non-acidic capping group.

For example, an article of manufacture for dispensing a perfume or fine fragrance, said article comprising a reservoir for containing a perfume or fine fragrance wherein said reservoir comprises at least one material which provides said liquid perfume or fine fragrance which is contained within said reservoir, and which contacts a surface of said reservoir, with a neutral or alkaline pH, said liquid perfume or fine fragrance comprising one or more of the pro-accords as described herein above.

The following are general, non-limiting examples of procedures for preparing pro-accords. Unless otherwise indicated, the materials obtained from the following examples are not preferred pro-accords nor pro-accords suitable for use in the preferred embodiments described herein.

EXAMPLE 1

Preparation of tris(phenylethyl)orthoformate

To a 500 mL single neck flask assembled with a short path distillation head and a magnetic stirrer is combined phenylethyl alcohol (66 g), triethyl orthoformate (20.2 g) and 3 drops of concentrated sulfuric acid under a nitrogen atmosphere. The reaction mixture is heated for 3 hr at 100° C. to distill over ethanol. The reaction progress is monitored by the amount of ethanol generated and by silica gel thin layer chromatography (TLC) eluting with 4% ethyl acetate/petroleum ether and development with iodine stain. Upon completion, the reaction mixture is diluted with diethyl ether (200 mL) and the organic phase washed three times with saturated aqueous sodium carbonate. The organic phase is dried over magnesium sulfate, filtered, and the resulting clear solution is concentrated in vacuo. The product is purified by kugelrohr distillation wherein the fraction in the range 120–140° C., at 0.1 mm Hg is collected to yield 47 g (91%). $^1$H NMR (CDCl$_3$); δ 7.2 (m, 15H); 5.0 (s, 1H); 3.6 (t, 6H); and 2.8 (t, 6H); $^{13}$C NMR (CDCl$_3$); δ 138.61, 128.81, 128.17, 126.10, 112.52, 64.76, and 35.89.

EXAMPLE 2

Preparation of tris(9-decenyl)orthoformate

The procedure described above is suitable for use in preparing tris(9-decenyl)orthoformate using 9-decenol (42.5 g, Rosalva-IFF), and triethyl orthoformate (10 g), to yield 27g (83%) of a clear oil isolated by kugelrohr distillation within the range 140–150° C., at 0.1 mm Hg. $^1$H NMR (CDCl$_3$)δ 5.8 (m, 3H); 5.1 (s, 1H); 4.9 (m, 6H); 3.5 (t, 6H); 2.0 (m, 6H); 1.6 (m, 6H); and 1.35 (m, 30H); $^{13}$C NMR (CDCl$_3$) δ 138.87, 113.89, 112.47, 67.74, 33.56, 29.28, 29.19, 29.15, 28.84, 28.68, and 25.52.

EXAMPLE 3

Preparation of tris(cis-3-hexenyl)orthoformate

The procedure described above is suitable for use in preparing tris(cis-3-hexenyl)orthoformate using cis-3-hexenol (115 g), and triethyl orthoformate (42.7 g) to yield 79 g (88%) of a clear oil isolated by kugelrohr distillation at 100° C., 0.1 mm Hg. $^1$H NMR (CDCl$_3$) δ 5.45 (m, 3H); 5.35 (m, 3H); 5.2 (s, 1H); 3.5 (t, 6H) 2.35 (d, t, 6H); 2.05 (d, t, 6H), and 1.0 (t, 9H); $^{13}$C NMR (CDCl$_3$) δ 133.57, 124.46, 112.31, 63.51, 27.36, 20.39, and 13.99.

EXAMPLE 4

Preparation of tris(geranyl/neryl) orthoformate

To a 500 mL single neck flask equipped with a short path distillation head and a magnetic stirrer is combined a mixture of geraniol and nerol (52 g, Bush Boake Allen 70/30), triethyl orthoformate (10 g) and anhydrous citric acid (0.66 g) under a nitrogen atmosphere. (The use of citric acid prevents undesired decomposition of the product). The reaction mixture is heated for 4 hr at 100° C. during which time ethanol is removed via distillation. The reaction progress is monitored by the amount of ethanol generated and by silica gel thin layer chromatography (TLC) eluting with 4% ethyl acetate/petroleum ether and development with iodine stain. Upon completion, the reaction mixture is diluted with diethyl ether (200 mL) and the organic phase washed three times with saturated aqueous sodium carbonate. The organic phase was dried over magnesium sulfate, filtered, and the resulting clear solution is concentrated in vacuo. The product is purified by kugelrohr distillation wherein the fraction in the range 140—150° C., at 0.1 mm Hg is collected to yield 23.5 g (73%). $^1$H NMR (CDCl$_3$) δ 5.35 (m, 3H); 5.25 (m, 1H); 5.1 (m, 3H); 4.15 (m, 6H); 2.1 (m, 12H); and 1.8–1.6 (m, 27H); $^{13}$C NMR (CDCl$_3$) δ 139.96, 139.75, 131.53, 131.25, 123.73, 123.59, 120.97, 119.99, 111.01, 60.40, 60.05, 39.31, 31.97, 26.48, 26.12, 25.39, 23.19, 17.37, and 16.14.

EXAMPLE 5

Preparation of tris(phenylethyl)orthoacetate

To a 250 mL three neck flask equipped with a rubber septum fitted with a needle, a drying tube charged with Drierite, a stopper, and equipped with a magnetic stirrer, is added phenylethyl alcohol (100 g), trimethylorthoacetate (30 g) and 3 drops of concentrated sulfuric acid. Nitrogen is slowly bubbled through the solution over a 4 day period to remove the methanol which is produced. The mixture is then diluted in diethyl ether (300 mL) and washed three times with saturated aqueous sodium carbonate. The organic phase is dried over magnesium sulfate, filtered, and the resulting clear solution is concentrated. The product is purified by kugelrohr distillation wherein the fraction in the range 150–170° C., at 0.1 mm Hg is collected to yield 72 g (74%). $^1$H NMR (CDCl$_3$) δ 7.2 (m, 15H); 3.6 (t, 6H); 2.8 (t, 6H); and 1.4 (s, 3H); $^{13}$C NMR (CDCl$_3$) δ 138.92, 128.93, 128.15, 126.07, 114.18, 63.01, 36.26, and 20.20.

EXAMPLE 6

Preparation of tris(cis-3-hexenyl)orthoacetate

The procedure described above is suitable for use in preparing tris(cis-3-hexenyl)orthoacetate using cis-3-hexenol (65 g) and trimethyl orthoacetate (22.2 g) and para-toluenesulfonic acid monohydrate (0.35 g) over 5 days, to yield 38.6 g (64%) of a clear oil isolated by kugelrohr distillation within the range 110–120° C., at 0.1 mm Hg. $^1$H NMR (CDCl$_3$) δ 5.3 (m, 6H), 3.4 (t, 6H), 2.25 (d, t, 6H); 2.0 (d, t, 6H); 1.4 (s, 3H); and 0.9 (t, 9H); $^{13}$C NMR (CDCl$_3$) δ 133.73, 125.03, 113.80, 61.48, 27.54, 20.29, 19.92, and 13.94.

EXAMPLE 7

Preparation of bis(geranyl/neryl) vanillin acetal

To a 1 L single-neck flask equipped with a Dean-Stark trap, condenser, and magnetic stirrer under a nitrogen atmosphere is added vanillin (60 g), geraniol/nerol (182 g, Bush Boake Allen 70/30), anhydrous citric acid (3.78 g) and 400 mL benzene. The mixture is refluxed for 24 hr during which time 4 mL of water is isolated in the Dean-Stark trap. The trap is replaced with a Soxhlet extractor having a cup containing 300 mL of activated molecular sieves (3 Å) and the reaction is refluxed for an addition 24 hr. The reaction mixture is cooled and washed four times with saturated aqueous sodium carbonate. The organic phase is dried over magnesium sulfate, filtered, and the resulting clear solution is concentrated in vacuo. The product is purified by kugelrohr distillation wherein the fraction above 80° C., at 0.1 mm Hg is retained to yield 111 g (84%) of a yellow oil comprising three isomers. $^1$H NMR (CDCl$_3$) δ 7.1–6.9 (m, 3H); 5.75 (s,b, 1H); 5.5 (s, 1H); 5.35 (m, 2H); 5.10 (m, 2H); 4.1 (m, 4H), 3.85 (s, 3H); 2.1 (m, 8H); and 1.75–1.60 (ms, 18H); $^{13}$C NMR (CDCl$_3$) δ 146.25, 145.47, 140.21, 139.93, 131.63, 131.36, 130.93, 123.78, 123.63, 121.34, 120.39, 119.82, 113.64, 108.83, 100.04, 61.66, 61.55, 61.36, 55.66, 39.39, 32.04, 26.54, 26.17, 25.44, 23.28, 17.44, and 16.23.

EXAMPLE 8

Preparation of bis(phenylethyl)benzaldehyde acetal

To a 1 L single-neck flask equipped with a Dean-Stark trap, condenser, and magnetic stirrer under a nitrogen atmosphere is added benzaldehyde (31.5 g), phenylethyl alcohol (159.5 g), and para-toluenesulfonic acid monohydrate (1.46 g) and 320 mL toluene. The mixture is refluxed for 3 hr during which time 5 mL of water is isolated in the Dean-Stark trap and TLC analysis (4% ethyl acetate/petroleum ether as the eluent) indicates all of the benzaldehyde is consumed. Upon completion, the reaction mixture is diluted with diethyl ether (200 mL) and the organic phase washed three times with saturated aqueous sodium carbonate. The organic phase is dried over magnesium sulfate, filtered, and the resulting clear solution is concentrated in vacuo. The product is purified by kugelrohr distillation wherein the fraction above 70° C., 0.3 mm Hg is retained and yields 58.6 g (59%) of a clear-yellow oil. The material obtained is further purified by chromatography over silica gel (Merck 230–400 mesh) eluting with 4% ethyl acetate/1% triethyl amine/petroleum ether to give a clear oil. $^1$H NMR (CDCl$_3$) δ 7.3 (m, 115H); 5.5 (s, 1H); 3.6 (t, 4H); and 2.8 (t, 4H). $^{13}$C NMR (CDCl$_3$) δ 139.07, 128.97, 128.27, 128.10, 126.70, 126.15, 101.44, 66.08, and 36.34.

EXAMPLE 9

Preparation of tetrakis(phenylethyl)orthocarbonate

To a 250 mL three neck flask equipped with a rubber septum fitted with a needle, a drying tube charged with Drierite, a stopper, and equipped with a magnetic stirrer, is added phenylethyl alcohol (36.7 g), tretraethylorthocarbonate (9.84 g) and para-toluenesulfonic acid monohydrate (0.21 g). Nitrogen is slowly bubbled through the solution while stirring over 36 hr to remove the ethanol which is produced. The mixture is then diluted with diethyl ether (300 mL) and washed three times with saturated aqueous sodium carbonate. The organic phase is dried over magnesium sulfate, filtered, and concentrated. The product is purified by kugelrohr distillation wherein the fraction above 100° C., 0.1 mm Hg is retained to yield 12.8 g (50%) of a clear oil. $^1$H NMR (CDCl$_3$) δ 7.2 (m, 16H); 3.6 (t, 8H); and 2.8 (t, 8H); $^{13}$C NMR (CDCl$_3$) δ 138.84, 128.89, 128.11, 126.03, 119.57, 63.75, and 35.8.

Perfume Compositions

The following are examples of fine fragrance compositions which comprise pro-accords according to the present invention.

EXAMPLE 10

| Ingredients | weight % |
| --- | --- |
| Pro-Accord Component[1] | |
| Tris(geranyl) orthoformate[2] | 2.2 |
| Tris(geranyl) orthoacetate[3] | 1.8 |
| Tris(phenylethyl) orthoformate | 1.2 |
| cis-Jasmone bis(phenylethyl) acetal | 2.3 |
| Potassium carbonate[4] ethanol[5] | 3.2 |

-continued

| Ingredients | weight % |
| --- | --- |
| Fragrance Raw Material Component | |
| Phenyl acetaldehyde | 0.2 |
| Base notes[6] | 83.9 |
| Adjuncts[7] | 0.6 |
| Ethanol[8] | balance |

[1]Pro-accord having a "rose" characteristic.
[2]The term "geranyl" refers to a mixture of "geranyl and neryl".
[3]The term "geranyl" refers to a mixture of "geranyl and neryl".
[4]Sufficient to provide 1 millimolar potassium carbonate reserve alkalinity.
[5]Ethanol carrier contains less than 1% water.
[6]Fragrance raw material base notes which includes polyethylene glycol as carrier.
[7]Jasmin Absolute derived from *Jasminum grandiflorum* L. (Oreaceae).
[8]Anhydrous ethanol.

EXAMPLE 11

| Ingredients | weight % |
| --- | --- |
| Pro-Accord Component[1] | |
| Tris(geranyl) orthoformate | 0.9 |
| Tris(benzyl) orthoacetate | 0.8 |
| Tris(cis-3-hexenyl) orthoformate | 0.6 |
| Tris(9-decen-1-ol) orthoformate | 0.4 |
| Tris(phenylethyl) orthoformate | 0.5 |
| cis-Jasmone bis(phenylethyl) acetal | 1.1 |
| Potassium carbonate[2] ethanol[3] | 3.4 |
| Fragrance Raw Material Component | |
| Phenyl acetaldehyde | 0.2 |
| Base, middle and top notes[4] | 8.2 |
| Adjuncts[5] | 0.3 |
| Ethanol[6] | balance |

[1]Pro-accord having a "modified rose" characteristic.
[2]Sufficient to provide 1 millimolar potassium carbonate reserve alkalinity.
[3]Ethanol carrier contains less than 1% water.
[4]Fragrance raw material base, middle and top notes which includes polyethylene glycol as carrier and anhydrous ethanol as a diluent.
[5]Mixture of synthetic (-)-cis and (-)-trans-4-methyl-2-(2-methyl-1-propenyl) tetrahydropyran; rose oxide.
[6]Anhydrous ethanol.

EXAMPLE 12

| Ingredients | weight % |
| --- | --- |
| Pro-Accord Component[1] | |
| Tris(citronellyl) orthoformate | 1.1 |
| Tris(benzyl) orthoacetate | 0.8 |
| Tris(cis-3-hexenyl) orthoformate | 0.6 |
| Citronellyloxyacetaldehyde bis(citronellyl) acetal | 0.7 |
| Tris(phenylethyl) orthoacetate | 0.6 |
| α-Hexylcinnamaldehyde bis(phenylethyl) acetal | 0.6 |
| Potassium carbonate[2] ethanol[3] | 3.4 |
| Fragrance Raw Material Component | |
| Phenyl acetaldehyde | 0.2 |
| Base notes and fragrance raw materials[4] | 78.4 |
| Adjuncts[5] | 2.1 |
| Ethanol[6] | balance |

[1]Pro-accord having a "muguet" characteristic.
[2]Sufficient to provide 1 millimolar potassium carbonate reserve alkalinity.
[3]Ethanol carrier contains less than 1% water.
[4]Fragrance raw material base, middle and top notes which includes polyethylene glycol as carrier and anhydrous ethanol as a diluent.
[5]Diethyl phthalate as a fixative.
[6]Anhydrous ethanol.

EXAMPLE 13

| Ingredients | weight % |
| --- | --- |
| Pro-Accord Component | |
| Bis(citronellyl) linalyl orthoacetate | 6.0 |
| Tris(geranyl) orthoacetate | 0.4 |
| cis-Jasmone bis(phenylethyl) acetal | 0.3 |
| Potassium carbonate[1] ethanol[2] | 2.2 |
| Fragrance Raw Material Component | |
| Coriander | 0.2 |
| Methyl phenylcarbinyl acetate | 0.2 |
| Benzyl acetate | 1.5 |
| Galbanum oil[3] | 0.2 |
| Citrolal PG | 2.5 |
| Triplal[4] | 0.2 |
| Ethyl acetoacetate | 0.8 |
| Lindenol | 0.5 |
| γ-Methyl ionone | 2.0 |
| Cyclogalbanate | 0.2 |
| P. T. Bucinal | 3.5 |
| Iso E super | 2.5 |
| Galaxolide 50 DEP | 22.0 |
| Methyl dihydrojasmonate | 23.0 |
| Exaltolide | 3.5 |
| Hexyl cinnamic aldehyde | 2.0 |
| Helional | 1.5 |
| Ethyl brassylate | 9.0 |
| Ambrettolide | 0.2 |
| cis-3-Hexenyl salicylate | 2.5 |
| Lemon Wescorps XC | 0.2 |
| Indole[4] | 0.5 |
| Cetalox[4] | 1.0 |
| Dipropylene glycol | 8.0 |
| Violet Leaf Absolute[3] | 1.0 |
| Calone 1951[4] | 0.5 |
| Phenyl acetaldehyde[5] | 0.2 |
| Mayol | 2.0 |
| Ethanol[6] | balance |

[1]Sufficient to provide 1 millimolar potassium carbonate reserve alkalinity.
[2]Ethanol carrier contains less than 1% water.
[3]1% solution in dipropylene glycol carrier.
[4]10% solution in dipropylene glycol carrier.
[5]10% solution in polyethylene alcohol carrier.
[6]Anhydrous ethanol carrier.

TABLE II

| | weight % | |
| --- | --- | --- |
| Ingredients | 14 | 15 |
| Component 1 | | |
| Fragrance accord[1] | 14 | 28 |
| Ethanol | balance | balance |
| Component 2 | | |
| Nonadyl orthoformate | 0.8 | 1.6 |
| Mugetanol orthoformate | 2.1 | 4.2 |
| Osyrol orthoformate | 2.3 | 4.6 |
| Benzyl orthoacetate | 3.7 | 7.4 |
| 1 mM potassium carbonate in ethanol | balance | balance |

[1]A proprietary fragrance accord comprising one or more fragrance raw materials selected from the group consisting of alcohols, esters, ketones, aldehydes, alkenes, ethers, and mixtures thereof.

What is claimed is:

1. A perfume composition having extended fragrance character impressions, comprising:
    A) a pro-accord component comprising:
        i) one or more pro-accords formed from at least one fragrance raw material, said pro-accord releasing upon hydrolysis at least two fragrance raw materials selected from the group consisting of primary, secondary, and tertiary alcohols, aldehydes, ketones, esters, carbonates, and mixtures thereof, provided each pro-accord:
  a) is formed from at least one fragrance raw material having a molecular weight greater than or equal to about 100 g/mol;
  b) has a molecular weight greater than or equal to about 300 g/mol;
  c) has a molecular weight at least two times greater than the lowest molecular weight fragrance raw material which comprises said pro-accord;
  d) has a fragrance release half-life of greater than or equal to about 0.1 hours at pH 5.3 and less than or equal to about 12 hours at pH 2.5 when measured in $NaH_2PO_4$ buffer;
  ii) the balance carriers, stabilizers, and other adjunct ingredients whereby said pro-accord component is provided with an amount of reserve alkalinity equal to at least 0.001 molar NaOH; and
B) a fragrance raw material component comprising:
  i) a mixture of base note fragrances;
  ii) one or more top or middle note fragrances;
  iii) the balance carriers, fixatives, and other adjunct ingredients.

2. A composition according to claim 1 wherein the pro-accord is selected from the group consisting of acetals, ketals, orthoesters, orthocarbonates, and mixtures thereof.

3. A composition according to claim 2 wherein said pro-accord has the formula:

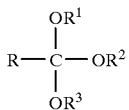

wherein R is hydrogen, $C_1$–$C_8$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof; $R^1$, $R^2$ and $R^3$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl, and mixtures thereof.

4. A composition according to claim 3 wherein R is hydrogen, methyl, ethyl, phenyl, and mixtures thereof; $R^1$, $R^2$, and $R^3$ are independently selected from the group consisting of 4-(1-methylethyl)cyclohexanemethyl, 2,4-dimethyl-3-cyclohexen-1-ylmethyl, 2,4-dimethylcyclohex-1-ylmethyl, 2,4,6-trimethyl-3-cyclohexen-1-ylmethyl, 2-phenylethyl, 1-(4-isopropylcyclohexyl)ethyl, 2,2-dimethyl-3-(3-methylphenyl)propan-1-yl, 3-phenyl-2-propen-1-yl, 2-methyl-4-(2,2,3-trimethyl-3-cyclopenten-1-yl)-2-buten-1-yl, 3-methyl-5-phenylpentan-1-yl, 3-methyl-5-(2,2,3-trimethyl-3-cyclopenten-1-yl)-4-penten-2-yl, 2-methyl-4-phenylpentan-1-yl, cis-3-hexen-1-yl, 3,7-dimethyl-6-octen-1-yl, 3,7-dimethyl-2,6-octadien-1-yl, 7-methoxy-3,7-dimethyloctan-2-yl, 6,8-dimethylnonan-2-yl, cis-6-nonen-1-yl, 2,6-nonadien-1-yl, 4-methyl-3-decen-5-yl, benzyl, 2-methoxy-4-(1-propenyl)phenyl, 2-methoxy-4-(2-propenyl)phenyl, and mixtures thereof.

5. A composition according to claim 3 wherein said pro-accord releases a fragrance raw material alcohol selected from the group consisting of 4-(1-methylethyl)cyclohexanemethanol, 2,4-dimethyl-3-cyclohexen-1-ylmethanol, (2,4-dimethylcyclohex-1-yl)methanol, (2,4,6-trimethyl-3-cyclohexen-1-yl)methanol, 2-phenylethanol, 1-(4-isopropylcyclohexyl)-ethanol, 2,2-dimethyl-3-(3-methylphenyl)propan-1-ol, 3-phenyl-2-propen-1-ol, 2-methyl-4-(2,2,3-trimethyl-3-cyclopenten-1-yl)-2-buten-1-ol, 3-methyl-5-phenylpentan-1-ol, 3-methyl-5-(2,2,3-trimethyl-3-cyclopenten-1-yl)-4-penten-2-ol, 2-methyl-4-phenylpentan-1-ol, cis-3-hexen-1-ol, 3,7-dimethyl-6-octen-1-ol, 3,7-dimethyl-2,6-octadien-1-ol, 7-methoxy-3,7-dimethyloctan-2-ol, 6,8-dimethylnonan-2-ol, cis-6-nonen-1-ol, 2,6-nonadien-1-ol, 4-methyl-3-decen-5-ol, benzyl alcohol, 2-methoxy-4-(1-propenyl)phenol, 2-methoxy-4-(2-propenyl)phenol, and mixtures thereof.

6. A composition according to claim 3 wherein said pro-accord compound releases a fragrance raw material ester having the formula:

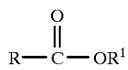

wherein R is hydrogen, methyl, ethyl, phenyl, and mixtures thereof; $R^1$ is selected from the group consisting of 4-(1-methylethyl)cyclohexanemethyl, 2,4-dimethyl-3-cyclohexen-1-ylmethyl, 2,4-dimethylcyclohex-1-ylmethyl, 2,4,6-trimethyl-3-cyclohexen-1-ylmethyl, 2-phenylethyl, 1-(4-isopropylcyclohexyl)ethyl, 2,2-dimethyl-3-(3-methylphenyl)propan-1-yl, 3-phenyl-2-propen-1-yl, 2-methyl-4-(2,2,3-trimethyl-3-cyclopenten-1-yl)-2-buten-1-yl, 3-methyl-5-phenylpentan-1-yl, 3-methyl-5-(2,2,3-trimethyl-3 -cyclopenten-1-yl)-4-penten-2-yl, 2-methyl-4-phenylpentan-1-yl, cis-3-hexen-1-yl, 3,7-dimethyl-6-octen-1-yl, 3,7-dimethyl-2,6-octadien-1-yl, 7-methoxy-3,7-dimethyloctan-2-yl, 6,8-dimethylnonan-2-yl, cis-6-nonen-1-yl, 2,6-nonadien-1-yl, 4-methyl-3-decen-5-yl, benzyl,2-methoxy-4-(1-propenyl)phenyl, 2-methoxy-4-(2-propenyl)phenyl, and mixtures thereof.

7. A composition according to claim 2 wherein said pro-accord is an acetal or a ketal having the formula:

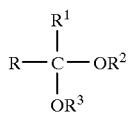

wherein R is $C_3$–$C_{20}$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof, $R^1$ is hydrogen or R; $R^2$ and $R^3$ are each independently selected from the group consisting of $C_5$–$C_{20}$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ aryl, $C_7$–$C_{20}$ substituted aryl, and mixtures thereof.

8. A composition according to claim 2 wherein said pro-accord has the formula:

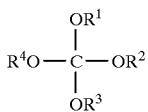

wherein $R^1$, $R^2$, $R^3$, and $R^4$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof.

9. A composition according to claim 8 wherein $R^1$, $R^2$, $R^3$, $R^4$ are independently 4-(1-methylethyl)cyclohexanemethyl, 2,4-dimethyl-3-cyclohexen-1-ylmethyl, 2,4-dimethylcyclohex-1-ylmethyl, 2,4,6-trimethyl-3-cyclohexen-1-ylmethyl, 2-phenylethyl, 1-(4-isopropylcyclohexyl)ethyl, 2,2-dimethyl-3-(3-methylphenyl)propan-1-yl, 3-phenyl-2-propen-1-yl, 2-methyl-4-(2,2,3-trimethyl-3-cyclopenten-1-yl)-2-buten-1-yl, 3-methyl-5-phenylpentan-1-yl, 3-methyl-5-(2,2,3-trimethyl-3-cyclopenten-1-yl)-4-penten-2-yl, 2-methyl-4-phenylpentan-1-yl, cis-3-hexen-1-yl, 3,7-dimethyl-6-octen-1-yl, 3,7-dimethyl-2,6-octadien-1-yl, 7-methoxy-3,7-dimethyloctan-2-yl, 6,8-dimethylnonan-2-yl, cis-6-nonen-1-yl, 2,6-nonadien-1-yl, 4-methyl-3-decen-5-yl, benzyl, 2-methoxy-4-(1-propenyl)phenyl, 2-methoxy-4-(2-propenyl)phenyl, and mixtures thereof.

10. An article of manufacture for dispensing a perfume or fine fragrance, said article comprising a reservoir for containing a perfume or fine fragrance wherein said reservoir comprises at least one material which provides said liquid perfume or fine fragrance which is contained within said reservoir, and which contacts a surface of said reservoir, with a neutral or alkaline pH, said liquid perfume or fine fragrance comprising:
  a) one or more pro-accords formed from at least one fragrance raw material, said pro-accord releases upon hydrolysis at least two fragrance raw materials selected from the group consisting of primary, secondary, and tertiary alcohols, aldehydes, ketones, esters, carbonates, and mixtures thereof, provided each pro-accord:
    i) is formed from at least one fragrance raw material having a molecular weight greater than or equal to about 100 g/mol;
    ii) has a molecular weight greater than or equal to about 300 g/mol;
    iii) has a molecular weight at least two times greater than the lowest molecular weight fragrance raw material which comprises said pro-accord;
    iv) has a fragrance release half-life of greater than or equal to about 0.1 hours at pH 5.3 and less than or equal to about 12 hours at pH 2.5 when measured in $NaH_2PO_4$ buffer;
  b) one or more top, middle, or base note fragrances; and
  c) carriers, fixatives, and other adjunct ingredients.

11. A fragrance delivery system comprising:
  a) a first component comprising:
    i) from about 0.1% to about 50% by weight, one or more fragrance raw materials;
    ii) the balance carriers and adjunct ingredients;
  b) a second component comprising:
    i) from about 0.5% to about 5% by weight, of nonadyl orthoformate;
    ii) from about 1.5% to about 5% by weight, of mugetanol orthoformate;
    iii) from about 1.5% to about 5% by weight, of osyrol orthoformate;
    iv) from about 1% to about 10% by weight, of one or more pro-accord orthoesters having the formula:

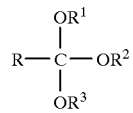

wherein R is hydrogen, $C_1$–$C_8$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof; $R^1$, $R^2$ and $R^3$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl, and mixtures thereof; and
    v) the balance carriers and adjunct ingredients.

12. A composition according to claim 11 wherein R is hydrogen, methyl, ethyl, propyl, and mixtures thereof, each $R^1$, $R^2$ and $R^3$ is and said second component further comprises from about 50% to about 93.8% of a non-aqueous 1 mM solution of an alkaline material, said alkaline material selected from the group consisting of sodium carbonate, potassium carbonate, lithium carbonate, calcium carbonate, magnesium carbonate, and mixtures thereof provided at least one of the pro-accord orthoesters from (b) has a fragrance release half life of less than or equal to about 12 hours at a pH 2.5 and greater than or equal to about 0.1 hour at pH 5.3 when measured in a $NaH_2PO_4$ buffer.

13. A fragrance delivery system comprising:
  a) a first component comprising:
    i) from about 0.1% to about 50% by weight, one or more fragrance raw materials;
    ii) the balance carriers and adjunct ingredients;
  b) a second component comprising:
    i) from about 0.8% to about 1.6% by weight, of nonadyl orthoformate;
    ii) from about 2.1% to about 4.2% by weight, of mugetanol orthoformate;
    iii) from about 2.3% to about 4.6% by weight, of osyrol orthoformate;
    iv) from about 1% to about 10% by weight, of one or more pro-accord orthoesters having the formula:

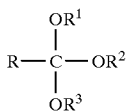

wherein R is hydrogen, $C_1$–$C_8$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof; $R^1$, $R^2$ and $R^3$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl, and mixtures thereof; and v) the balance 1 mM potassium carbonate in ethanol.

14. A fragrance delivery system comprising:

a) a first component comprising:
  i) from about 10% to about 50% by weight, a fragrance accord;
  ii) the balance ethanol;
b) a second component comprising:
  i) from about 0.8% to about 1.6% by weight, of nonadyl orthoformate;
  ii) from about 2.1% to about 4.2% by weight, of mugetanol orthoformate;
  iii) from about 2.3% to about 4.6% by weight, of osyrol orthoformate;
  iv) from about 3.7% to about 7.4% by weight, of benzyl orthoacetate; and
  v) the balance 1 mM potassium carbonate in ethanol.

15. An article of manufacture according to claim 10 further comprising a spray dispenser for delivery of said perfume or fine fragrance.

16. An article of manufacture for dispensing a perfume or fine fragrance, comprising:

A) a first reservoir containing:
  i) one or more pro-accords formed from at least one fragrance raw material, said pro-accord releasing upon hydrolysis at least two fragrance raw materials selected from the group consisting of primary, secondary, and tertiary alcohols, aldehydes, ketones, esters, carbonates, and mixtures thereof, provided each pro-accord:
    a) is formed from at least one fragrance raw material having a molecular weight greater than or equal to about 100 g/mol;
    b) has a molecular weight greater than or equal to about 300 g/mol;
    c) has a molecular weight at least two times greater than the lowest molecular weight fragrance raw material which comprises said pro-accord;
    d) has a fragrance release half-life of greater than or equal to about 0.1 hours at pH 5.3 and less than or equal to about 12 hours at pH 2.5 when measured in $NaH_2PO_4$ buffer;
  ii) carriers, stabilizers, and other adjunct ingredients whereby said pro-accord component is provided with an amount of reserve alkalinity equal to at least 0.001 molar NaOH;
B) a second reservoir containing:
  i) a mixture of base note fragrances;
  ii) one or more top or middle note fragrances;
  iii) carriers, fixatives, and other adjunct ingredients;
C) a first spraying device affixed to said first reservoir for the purpose of measurably delivering the composition of said first reservoir to human skin; and
D) a second spraying device affixed to said second reservoir for the purpose of measurably delivering the composition of said second reservoir to human skin.

* * * * *